US006833351B2

(12) United States Patent
Dieterich

(10) Patent No.: US 6,833,351 B2
(45) Date of Patent: Dec. 21, 2004

(54) METHOD OF TREATING ANEMIA CAUSED BY RIBAVIRIN TREATMENT OF HEPATITIS C USING ERYTHROPOIETIN ALPHA

(76) Inventor: Douglas T. Dieterich, 62 St. James St. South, Garden City, NY (US) 11530

( * ) Notice: Subject to any disclaimer, the term of this patent is extended or adjusted under 35 U.S.C. 154(b) by 138 days.

(21) Appl. No.: 09/862,404

(22) Filed: May 21, 2001

(65) Prior Publication Data

US 2003/0032590 A1 Feb. 13, 2003

(51) Int. Cl.$^7$ .................. A61K 38/00; A61K 31/7084; C07K 14/56; C07K 14/505
(52) U.S. Cl. ............................. 514/2; 514/44; 514/45; 530/385; 530/395; 530/399
(58) Field of Search ............................. 514/2, 44, 45; 530/385, 395, 399, 350, 351; 512/2, 43

(56) References Cited

U.S. PATENT DOCUMENTS

| | | | |
|---|---|---|---|
| 5,399,551 | A | 3/1995 | Ise et al. |
| 5,543,390 | A | 8/1996 | Yatvin et al. |
| 5,543,391 | A | 8/1996 | Yatvin et al. |
| 5,604,198 | A | 2/1997 | Poduslo et al. |
| 5,610,054 | A | 3/1997 | Draper |
| 5,661,125 | A | 8/1997 | Strickland |
| 5,670,477 | A | 9/1997 | Poduslo et al. |
| 5,869,253 | A | 2/1999 | Draper |
| 6,063,772 | A | 5/2000 | Tam |
| 6,132,966 | A | 10/2000 | Draper |
| 6,172,046 | B1 | 1/2001 | Albrecht |
| 6,268,336 | B1 * | 7/2001 | Niitsu et al. .................. 514/8 |

OTHER PUBLICATIONS

Perez–Olmeda et al. Interferon plus ribavirin in HIV–infected patients with chronic hepatitis C. Abstract, Journal of Acquired Deficiency Syndromes 22(3), pp. 308–309 (1999).*

Bruchfeld et al. Management of ribavirin treatment in renal insufficiency and dialysis. Journal of the American Society of Nephrology, Sep., 2000, vol., 11, No. Program and Abstract Issue, pp. 57A.*

Abels RI, Larholt KM, Krantz KD, et al., "Recombinant Human Erythropoietin (rHuEPO) for the Treatment of the Anemia of Cancer," *The Oncologist*, 1996, vol. 1, pp. 140–150.

Alter MJ, Kruszon–Moran D, Nainan OV, et al., "The Prevalence of Hepatitis C Virus Infection in the United States, 1988 Through 1994," *New England Journal of Medicine*, 1999, vol. 341, pp. 556–562.

Alter MJ, Mast EE, Moyer LA, et al., "Hepatitis C," *Infectious Disease Clinics of North America*, 1998, vol. 12, pp. 13–26.

Baer AN, Dessypris EN, Goldwasser E, et al., "Blunted Erythropoietin Response to Anaemia in Rheumatoid Arthritis," *British Journal of Haematology*, 1987, vol. 66, pp. 559–564.

Beguin Y, "Erythropoietin and the Anemia of Cancer," *Acta Clinica Belgica* 1996, vol. 51, pp. 36–52.

Causse X, Godinot H, Chevallier M, et al., "Comparison of 1 or 3 MU of Interferon Alfa–2b and Placebo in Patients with Chronic Non–A, Non–B Hepatitis," *Gastroenterology*, 119, vol. 101, pp. 497–502.

Cazzola M, Mercuraili F, Brugnara C, "Use of Recombinant Human Erythropoietin Outside the Setting of Uremia," *Blood*, 1997, Vo. 89, pp. 4248–4267.

Davis GL, Balart LA, Schiff ER, et al., "Treatment of Chronic Hepatitis C with Recombinant Interferon Alfa: A Multicenter Randomized, Controlled Trial," *New England Journal of Medicine*, 1989, vol. 321, pp. 1501–1506.

Dawson–Suander B, Trapp RG, *Basic and Clinical Biostatistics*, Appleton & Lange, Norwalk, CT, 1990*.

Di Bisceglie AM, Martin P, Kassianides C, et al., "Recombinant Interferon Alfa Therapy for Chorinic Hepatitis C: A Randomized, Double–Blind–Placebo–Controlled Trial," *New England Journal of Medicine*, 1989, vol. 321, pp. 1506–1510.

Elghetany MT, Davey FR, "Erythrocytic Disorders," *Clinical Diagnosis and Management by Laboratory Methods*, 19$^{th}$ Ed. (Henry JB, ed.), WB Saunders Company, Philadelphia, 1996, pp. 617–663.

Fisher JW, "Erythropoietin: Physiologic and Pharmacologic Aspects," *Proceedings of the Society for Experimental Biology and Medicine*, 1997, vol. 216, pp. 358–369.

Gogu SR, Beckman BS, Wilson RB, et al., "Inhbitory Effects of Zidovudine in Erythroid Progenitor Cells: Reversal with a Combination of Erythropoietin and Interleukin–3," *Biochemical Pharmacology*, 1995, vol. 50, pp. 413–419.

Goodnough LT, Anderson KC, Kurtz S, et al., "Indications and Guidelines for the Use of Hematopoietic Growth Factors," *Transfusion*, 1993, vol. 33, pp. 944–959.

Harbol, AW. Liesveld JL, Simpson–Haidaris PJ, et al., "Mechanisms of Cytopenia in Human Immunodeficiency Virus Infection," *Blood Reviews*, 1994, vol. 8, pp. 241–251.

(List continued on next page.)

*Primary Examiner*—Gary Kunz
*Assistant Examiner*—Regina M. DeBerry
(74) *Attorney, Agent, or Firm*—Frommer Lawrence & Haug LLP

(57) ABSTRACT

Claimed and disclosed is a new use for a previously approved drug: erythropoietin. The present invention teaches using Erythropoetin to treat anemia caused by the combined treatment of Ribavirin and alpha-interferon. Erythropoetin has previously been approved for the treatment of anemia caused by cancer chemotherapy, renal failure and HIV. It has not been used for anemia caused by ribavirin. Ribavirin is part of a two-drug regimen now used to treat hepatitis C along with alpha interferon. The principal side effect of ribavirin is a hemolytic anemia. In the past, mangement of that anemia was done by dose reduction of the ribavirin, sometimes resulting in reversal of part of the anemia. It has become particularly important in light of new data, to maximize the dose of ribavirin given to persons undergoing treatment for hepatitis C to ensure a successful eradication of hepatitis C.

11 Claims, 19 Drawing Sheets

OTHER PUBLICATIONS

Jelkmann WB, Fandrey J, Frede S, et al., "Inhibition of Erythropoietin Production by Cytokines: Implications for the Anemia Involved in Inflammatory States," *Annals of the New York Academy of Sciences,* 1994, vol. 718, pp. 300–309.

Jen F, Glue P, Gupta S, et al., "Population Pharmacokinetic and Pharmacodynamic Analysis of Ribavirin in Patients with Chronic Hepatitis C," *Therapeutic Drug Monitoring,* vol. 22, No. 3, 2000.

Koziel MJ, "Cytokines in Viral Hepatitis," *Seminars in Liver Disease,* 1999, vol. 19, pp. 157–169.

Krantz SB, "Erythropoietin," *Blood,* 1991, vol. 77, pp. 419–434.

Kuehl AK, Noormohamed SE, "Recombinant Erythropoietin for Zidovudine–Induced Anemia in AIDS," *Annals of Pharmacotherapy,* 1995, vol. 29, pp. 778–779.

Lai CM, Swaminathan N, Beilharz MW, et al., "Interferon–α Inhibits Erythropoietin–Induced Proliferation, but Not Differentiation, and Restricts Erythroleukemia Development," *Journal of Interferon & Cytokine Research,* 1995, vol. 15, pp. 669–675.

MacDougall DS, "Recombinant Human Erythropoietin for HIV–Related Anemia," *Journal of the Int'l Association of Physicians in AIDS Care,* Oct. 1998, pp. 18–24.

Marcellin P, Boyer N, Giostra E, et al., "Recombinant Human α–Interferon in Patients with Chronic Non–A, Non–B Hepatitis: A Multicenter Randomized Controlled Trial from France." *Hepatology,* 1991, vol. 13, pp. 393–397.

McHutchison JG, Gordon SC, Schiff ER, et al., "Interferon Alfa–2b Alone or in Combination With Ribavirin as Initial Treatment for Chronic Hepatitis C," *New England Journal of Medicine,* 1998, vol. 339, pp. 1485–1492.

Means RT, Jr., "Advances in the Anemia of Chronic Disease," *Int'l Journal of Hematology,* 1999, vol. 70, pp. 7–12.

Means RT, Jr., "Pathogenesis of the Anemia of Chronic Disease: A Cytokine–Mediated Anemia," *Stem Cells,* 1995, vol. 13, pp. 32–37.

Means RT, Jr., Krantz SB, "Progress in Understanding the Pathogenesis of the Anemia of Chronic Disease," *Blood,* 1992, vol. 80, pp. 1639–1647.

Moore RD, Keruly JC, Chaisson RE, "Anemia and Survival in HIV Infection," *Journal of Acquired Immune Deficiency Syndromes and Human Retrovirology,* 1998, vol. 19, pp. 29–33.

Musto P, Falcone A, D'Arena G, et al., "Clinical Results of Recombinant Erythropoietin in Transfusion–Dependent Patients with Refractor Multiple Myeloma: Role of Cytokines and Monitoring of Erythropoiesis," *European Journal of Haematology,* 1997, vol. 58, pp. 314–319.

Napoli J, Bishop GA, McGuinness PH, et al., "Progressive Liver Injury in Chronic Hepatitis C Infection Correlates with Increased Intrahepatic Expression of Th1–Associated Cytokines," *Hepatology,* 1996, vol. 24, pp. 759–765.

Peeters HM, Jongen–Lavrencic M, Vregdenhil G, et al., "Effect of Recombinant Human Erythropoietin on Anemia and Disease Activity in Patients with Rheumatoid Arthritis and Anemia of Chronic Disease: A Randomised Placebo Controlled Double Blind 52 Weeks Clinical Trial," *Annals of the Rheumatic Diseases,* 1996, vol. 55, pp. 739–744.

Poynard T, Marcellin P, Lee SS, et al., "Randomised Trial of Interferon α2b Plus Ribavirin for 48 Weeks of For 24 Weeks Versus Interferon α2b Plus Placebo for 48 Weeks for Treatment of Chronic Infection with Hepatitis C Virus," *Lancet,* 1998, vol. 352, pp. 1426–1432.

Reichard O, Norkrans G, Fryden A, et al., "Randomized, Double–Blind, Placebo–Controlled Trial of Interferon α–2b With and Without Ribavirin for Chronic Hepatitis C," *Lancet,* 1998, vol. 351, pp. 83–87.

Reichard O, Schvarez R, Weiland O., "Therapy of Hepatitis C: Alpha Interferon and Ribavirin," *Hepatology,* 1997, vol. 26 (Suppl 1), pp. 108S–111S.

Spivak JL, Barnes DC, Fuchs E, et al., "Serum Immunoreactive Erythropoietin in HIV–Infected Patients," *Journal of the American Medical Association,* 1989, vol. 261, pp. 3104–3107.

Thomas HC, Booth J, Brown J., "Pathophysiology and Treatment of Hepatitis C," *Drugs,* 1996, vol. 52 (Supp. 2), pp. 1–8.

Weisz K, Goldman D. Talal A, et al., "Interferon (IFN) and Ribavirin (RBV) Therapy for Hepatitis C (HCV) in HIV–Coinfected Patients, 12 Month Follow–Up," 7th Conference on Retroviruses and Opportunistic Infections, Jan. 30–Feb. 2, 2000, Abstract 283.

"Management of Hepatitis C Consensus Development Statement," National Institutes of Health, Mar. 24–26, 1997.

"Rebetron Product Label," *Physician's Desk Reference,* 53rd Ed., Medical Economics Company, Montvale, NJ, 1999.

\* cited by examiner

FIGURE 1

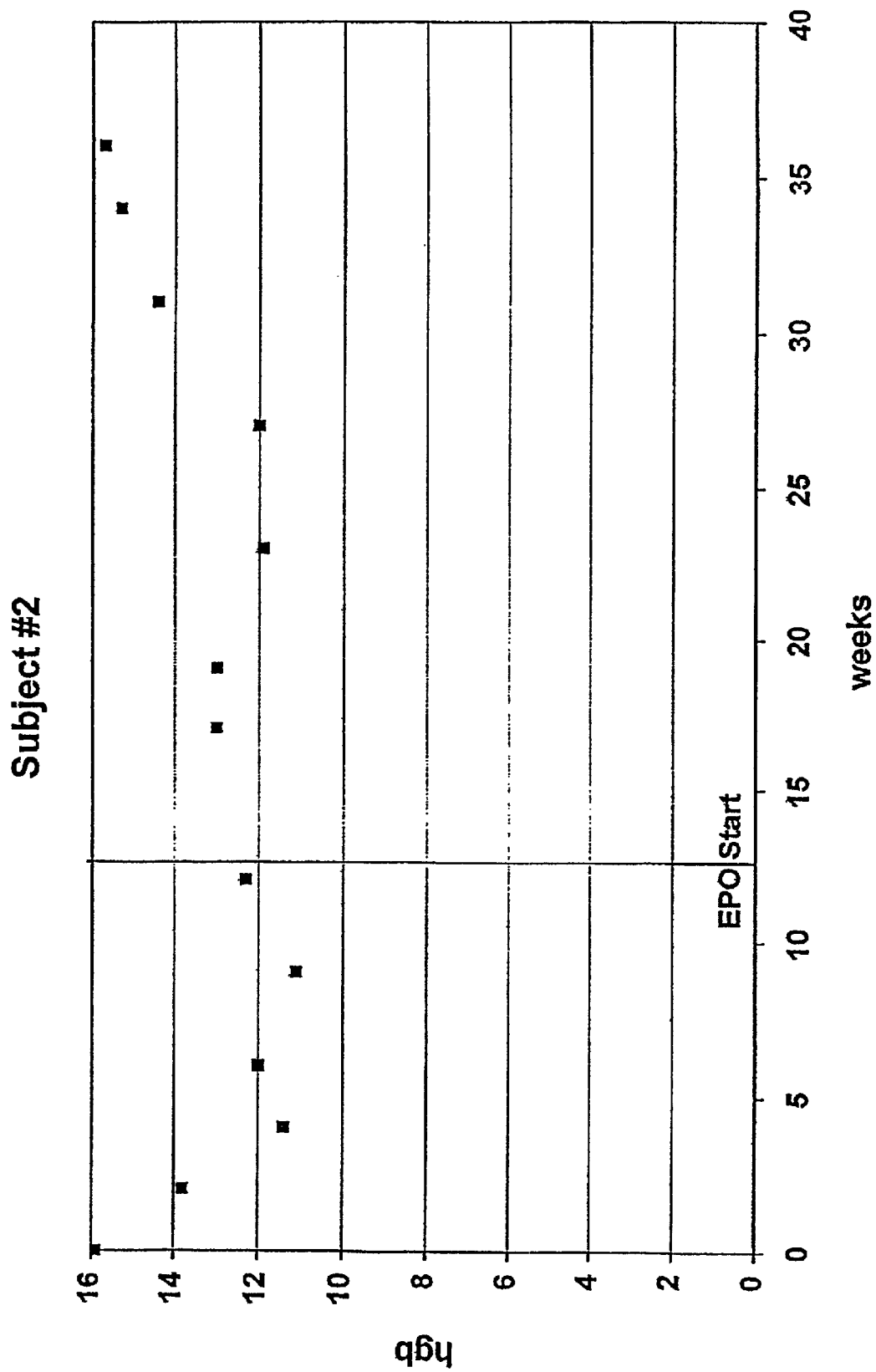
Figure 2.1

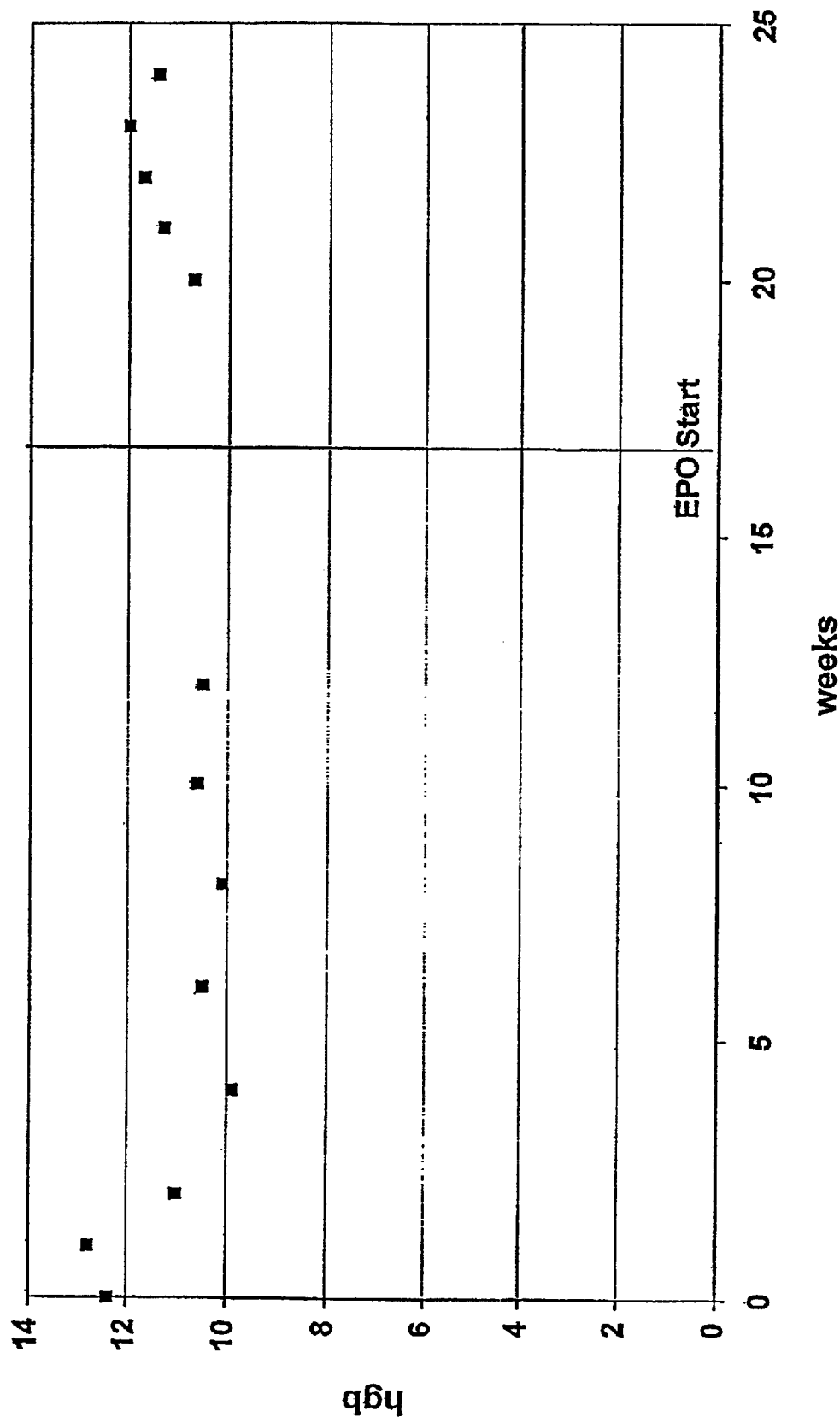
Figure 2.2

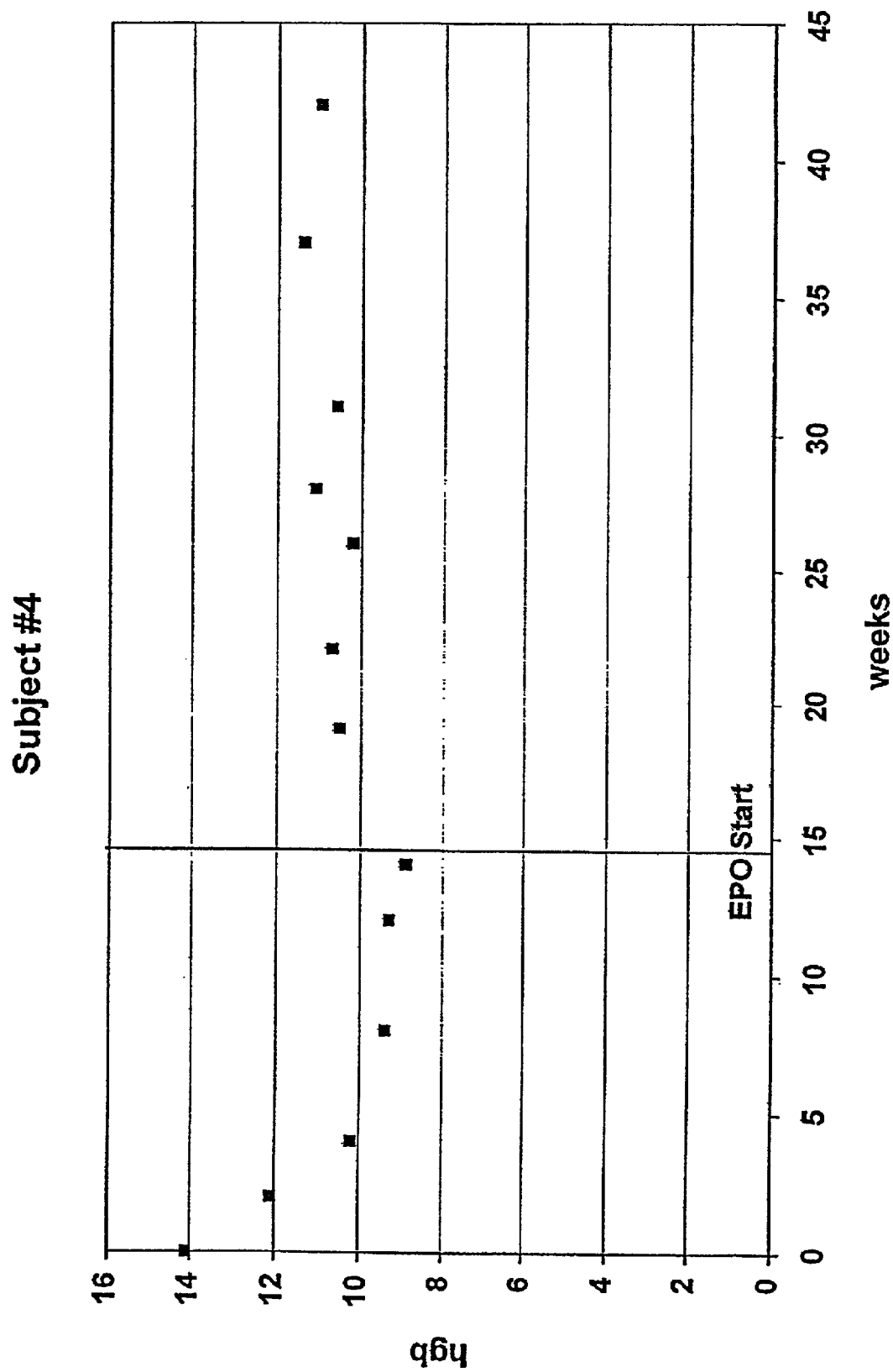
FIGURE 2.3

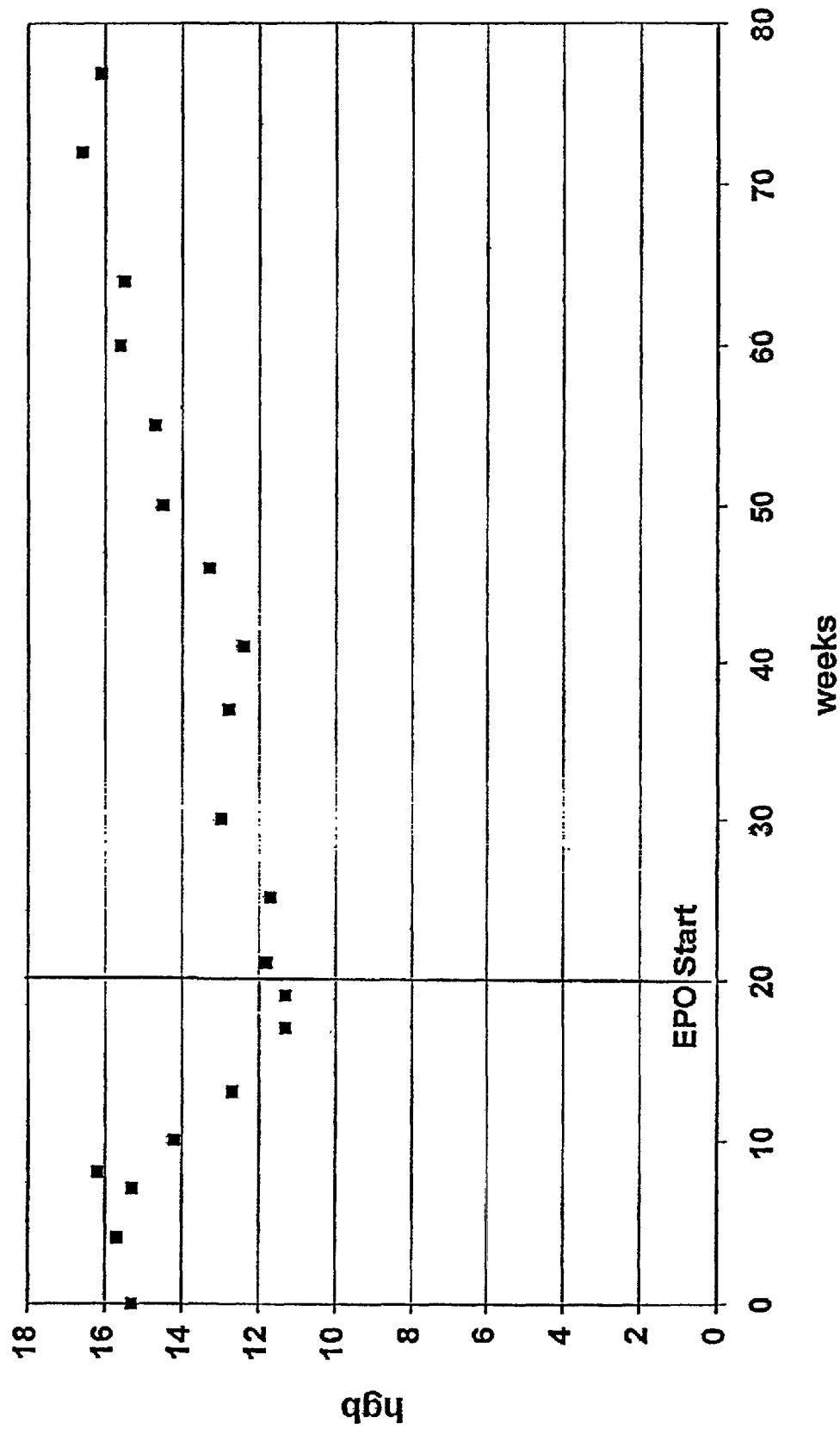
FIGURE 2.4

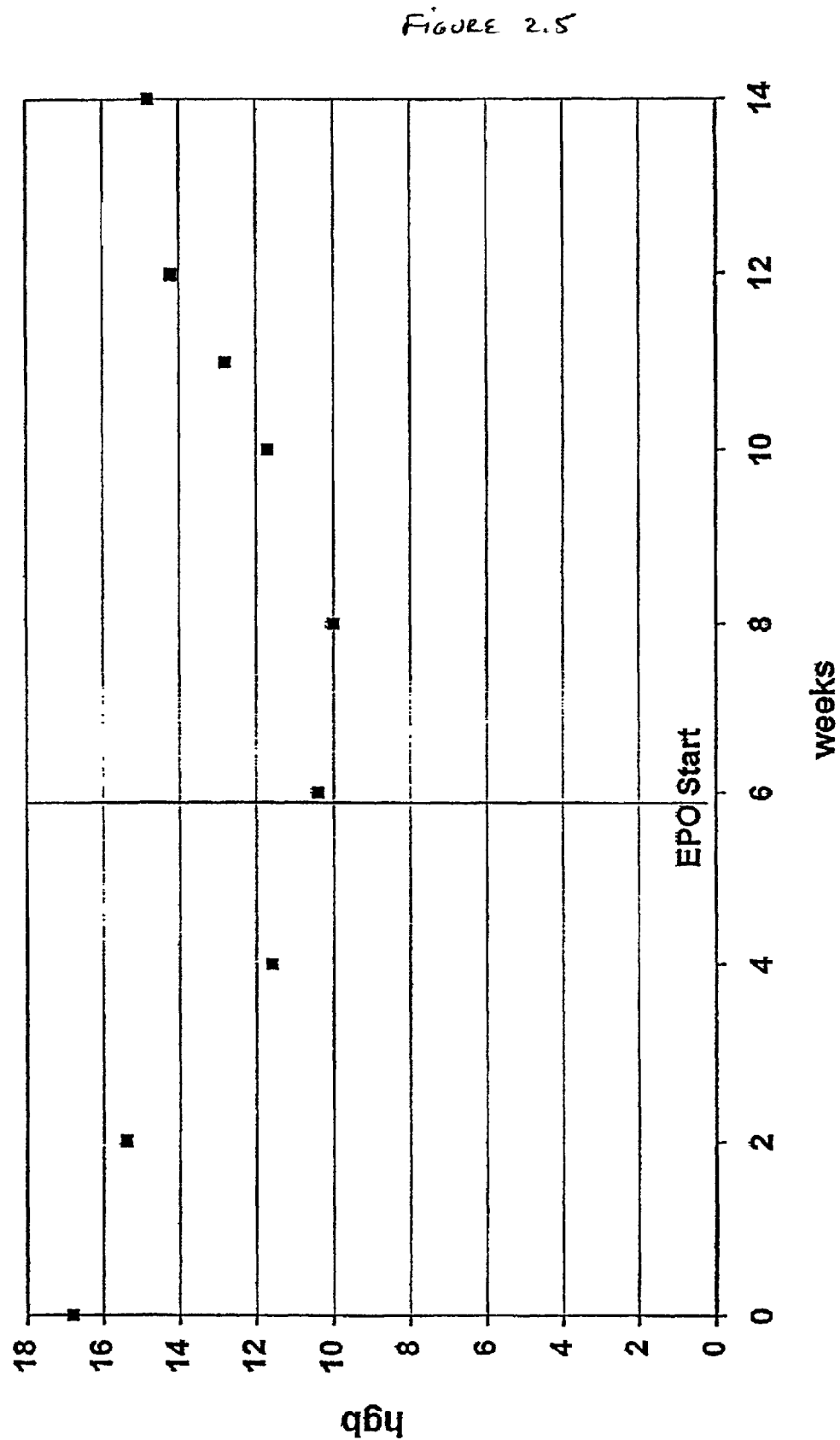
Figure 2.5

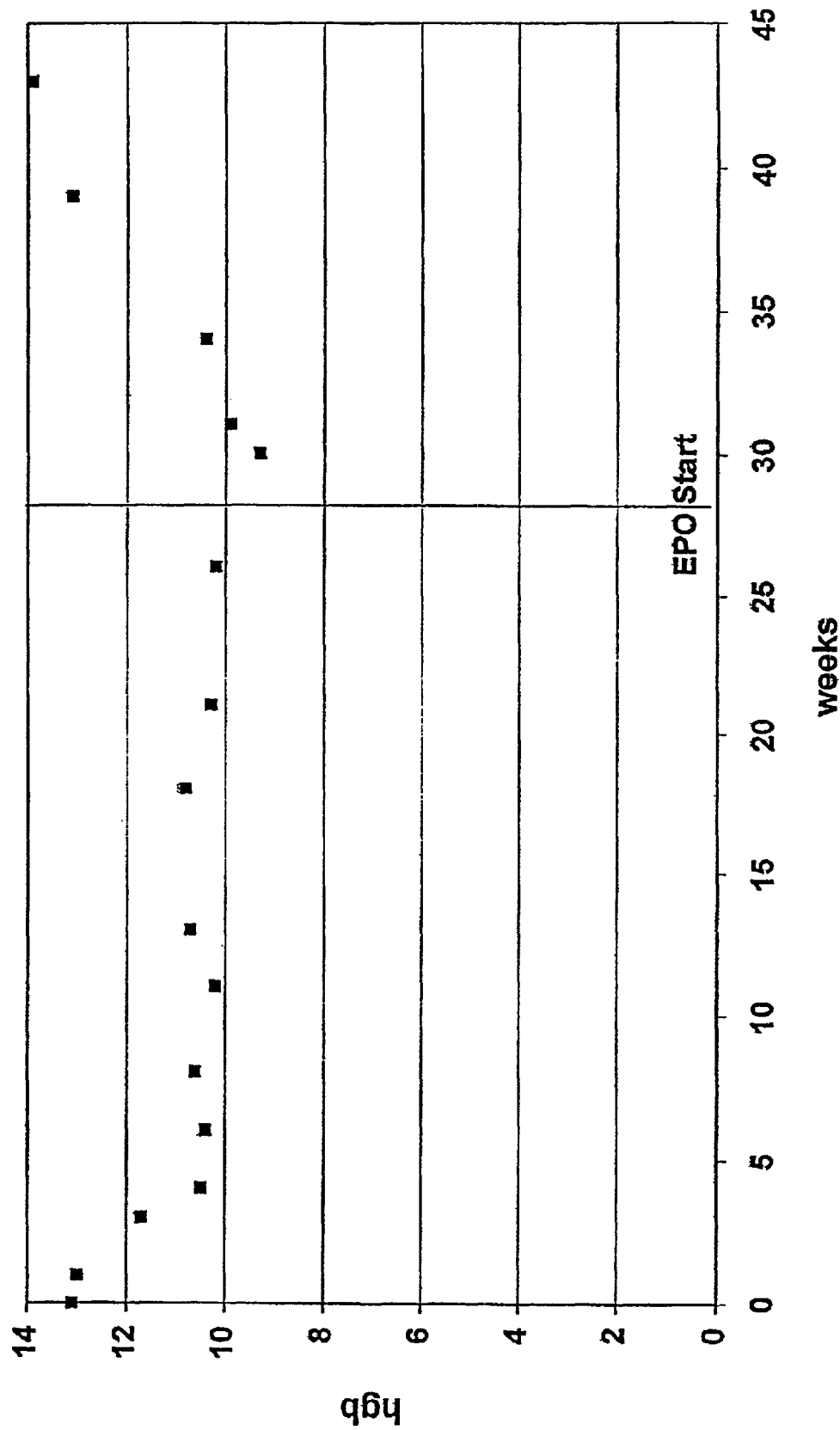
Figure 2.6

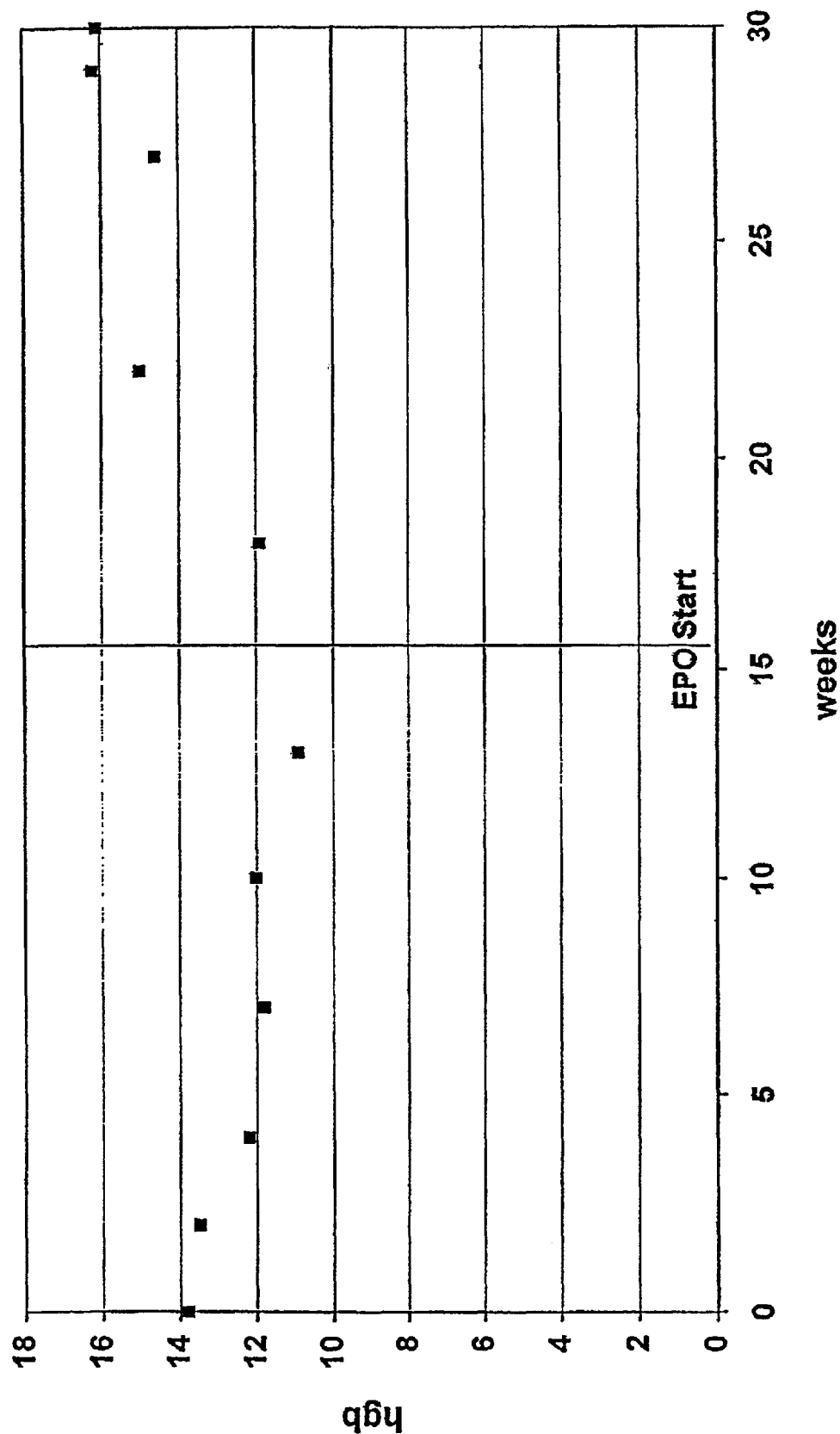
FIGURE 2.7

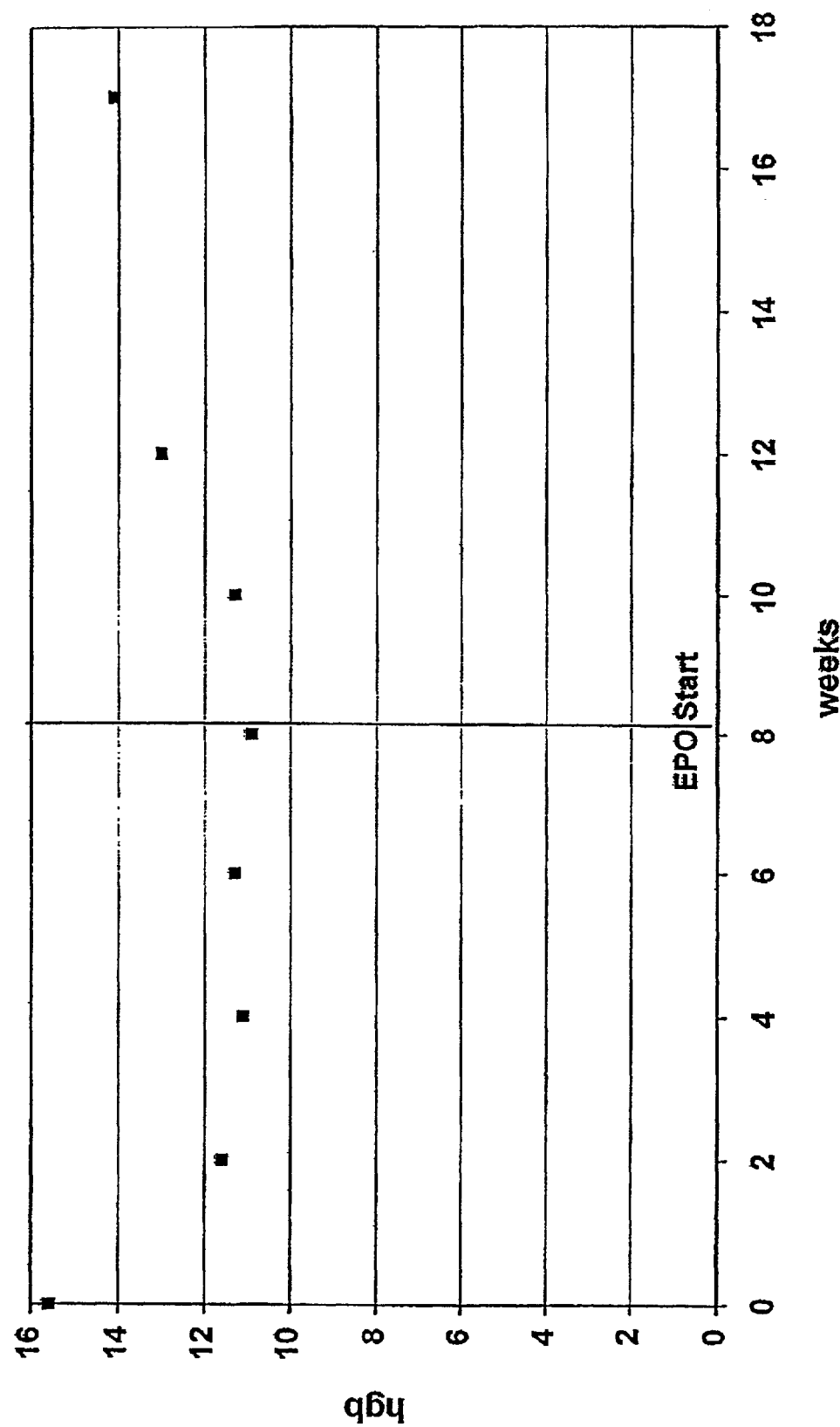

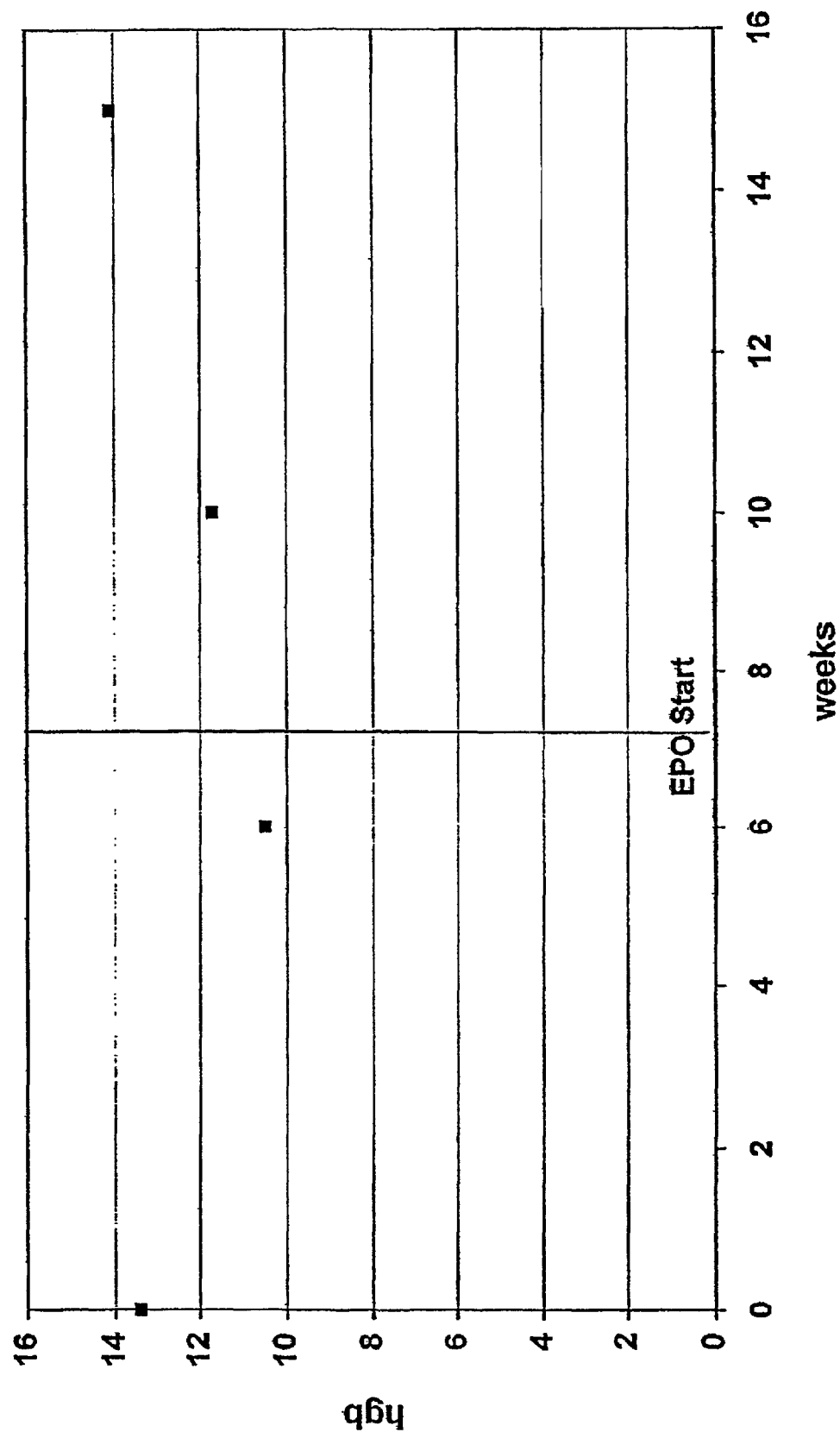
Figure 2.9

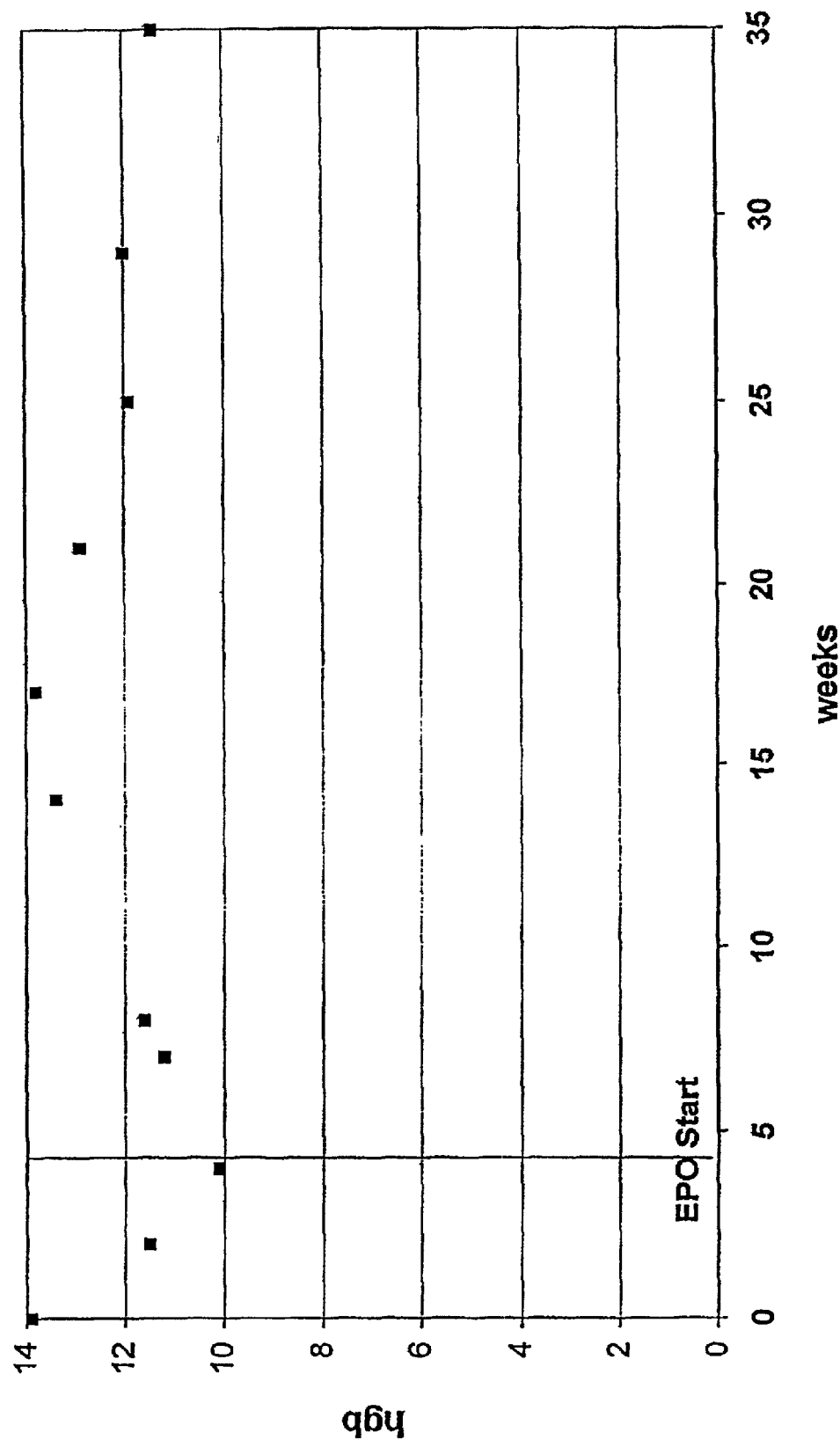
Figure 2.10

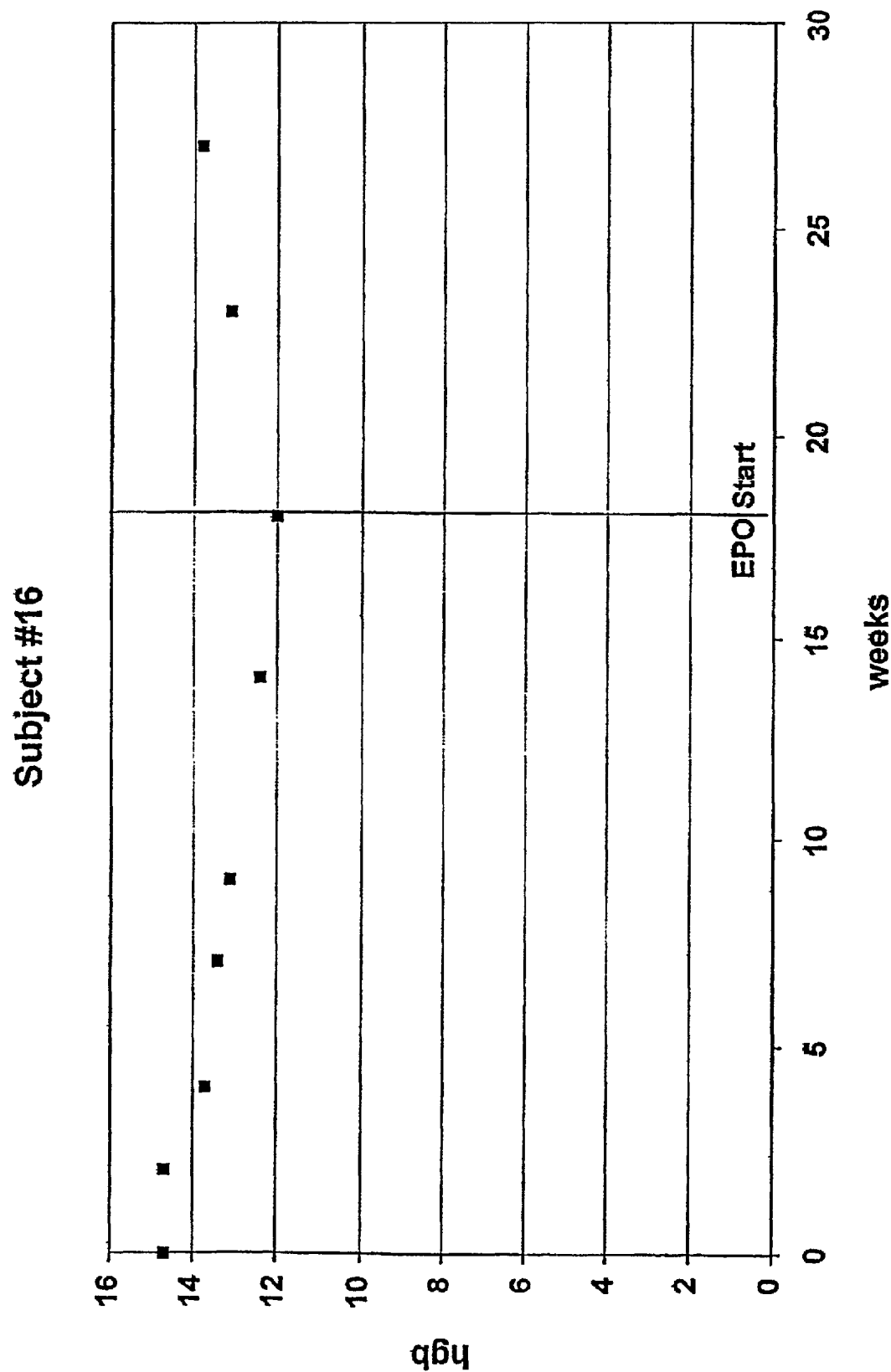
Figure 2.12

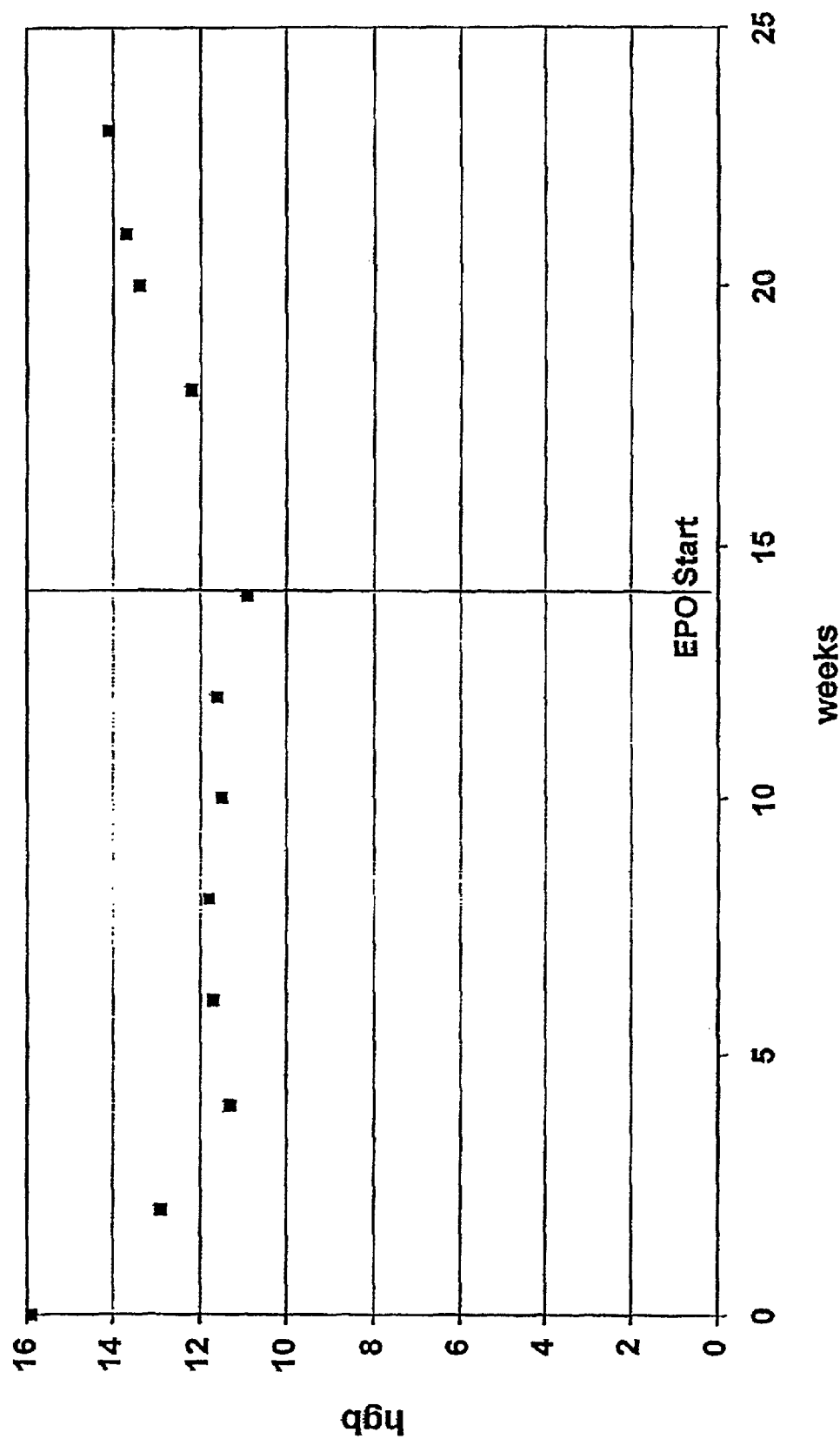
FIGURE 2.13

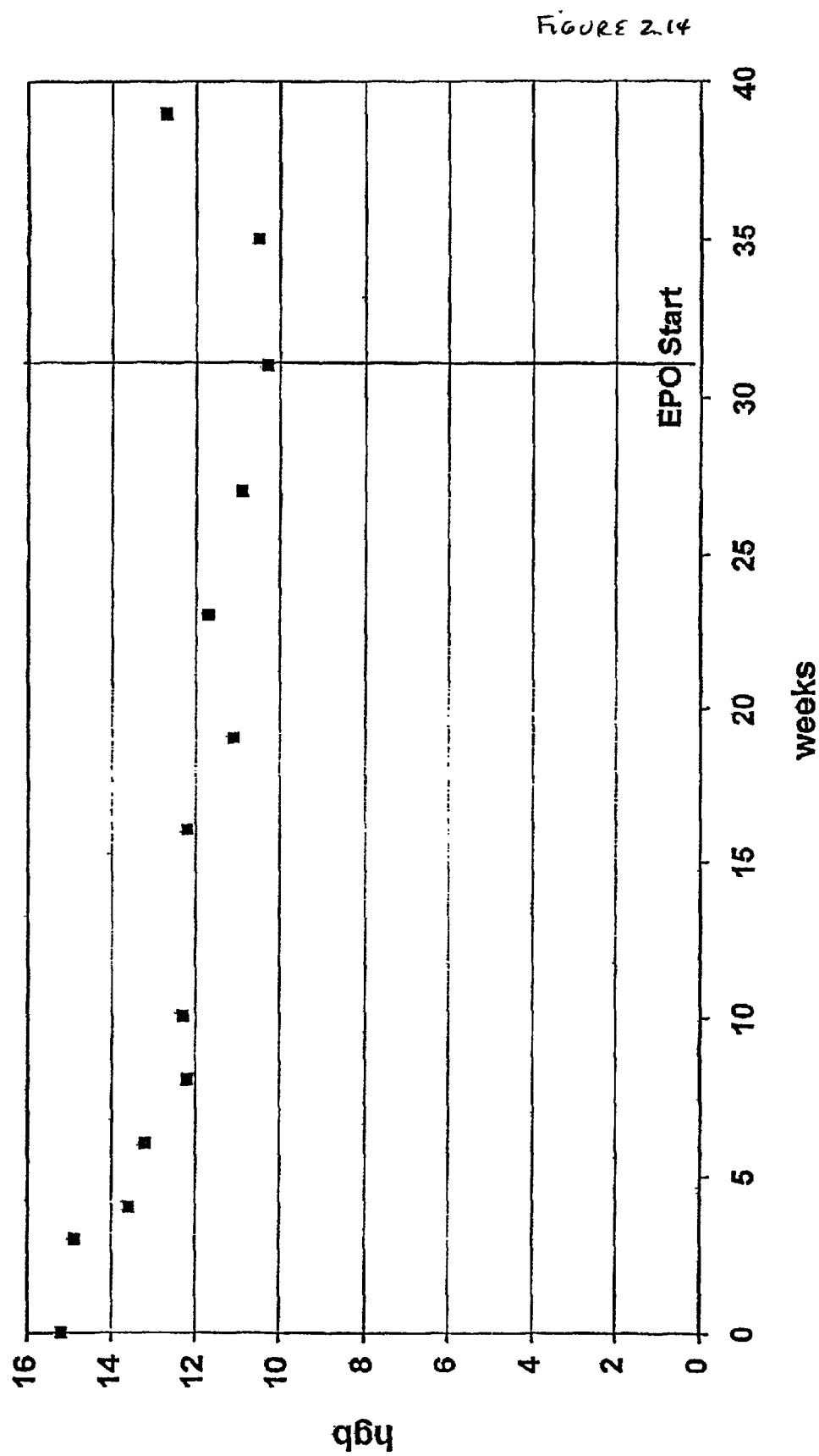
FIGURE 2.14

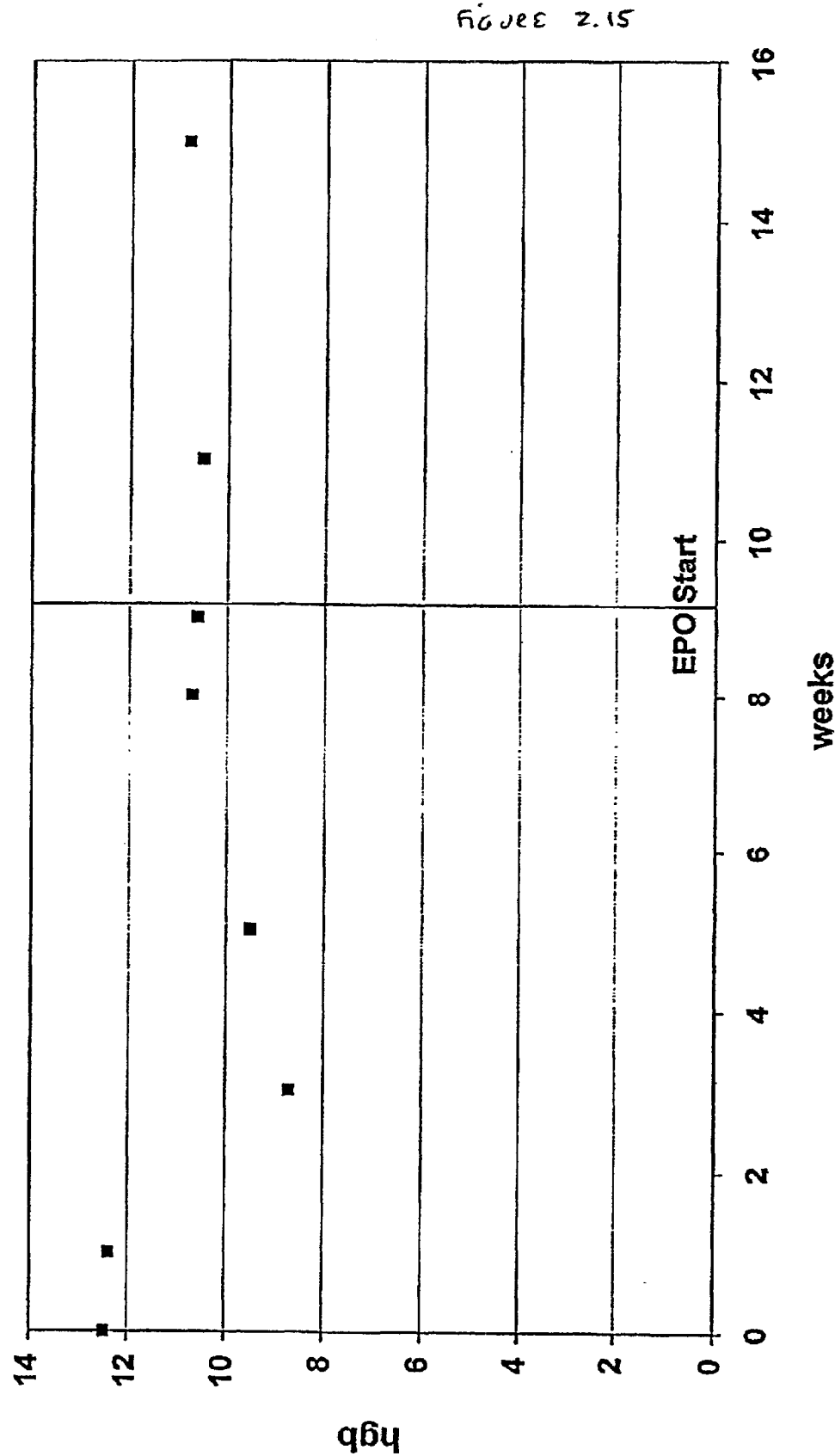
Figure 2.15

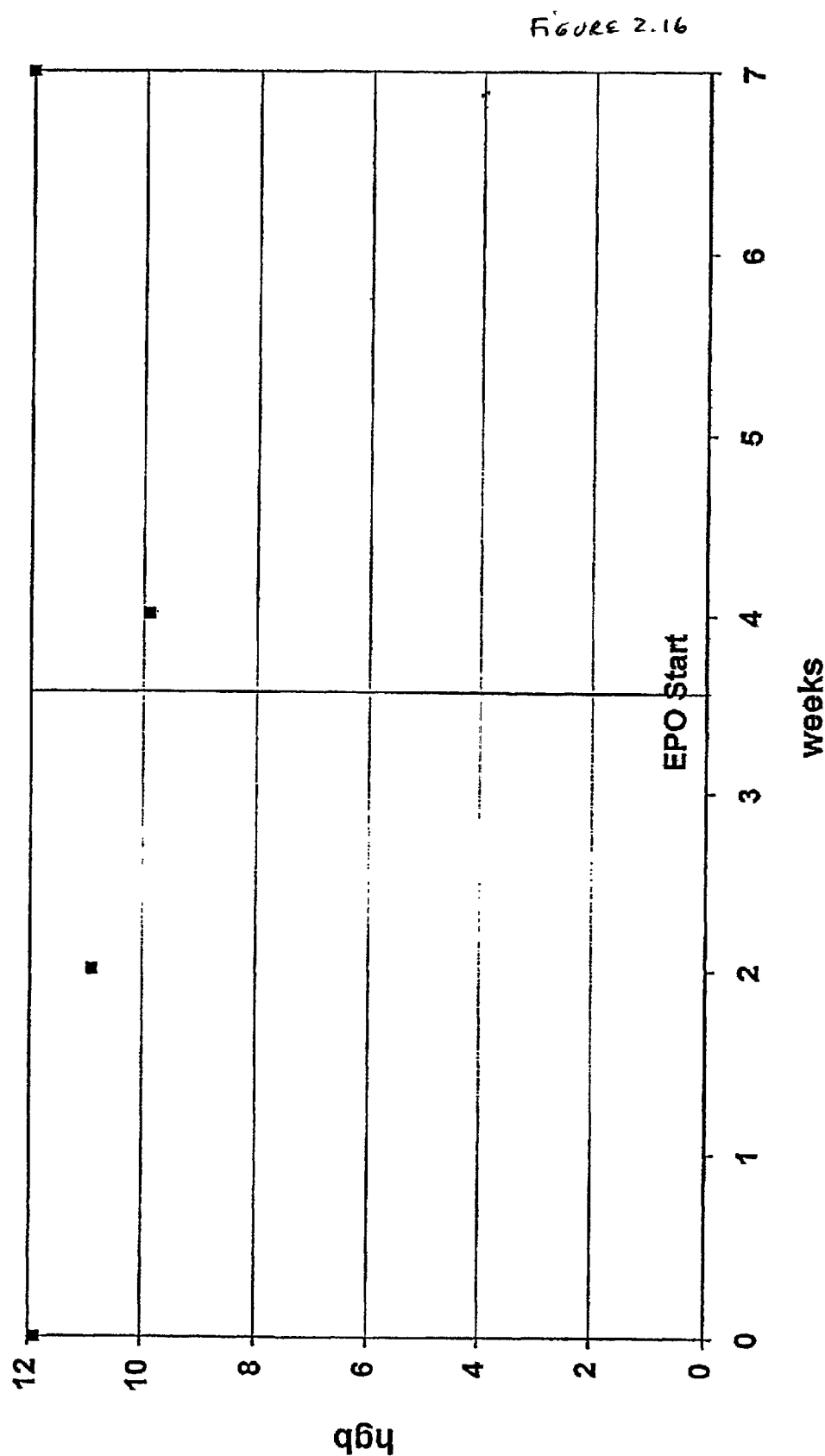
Figure 2.16

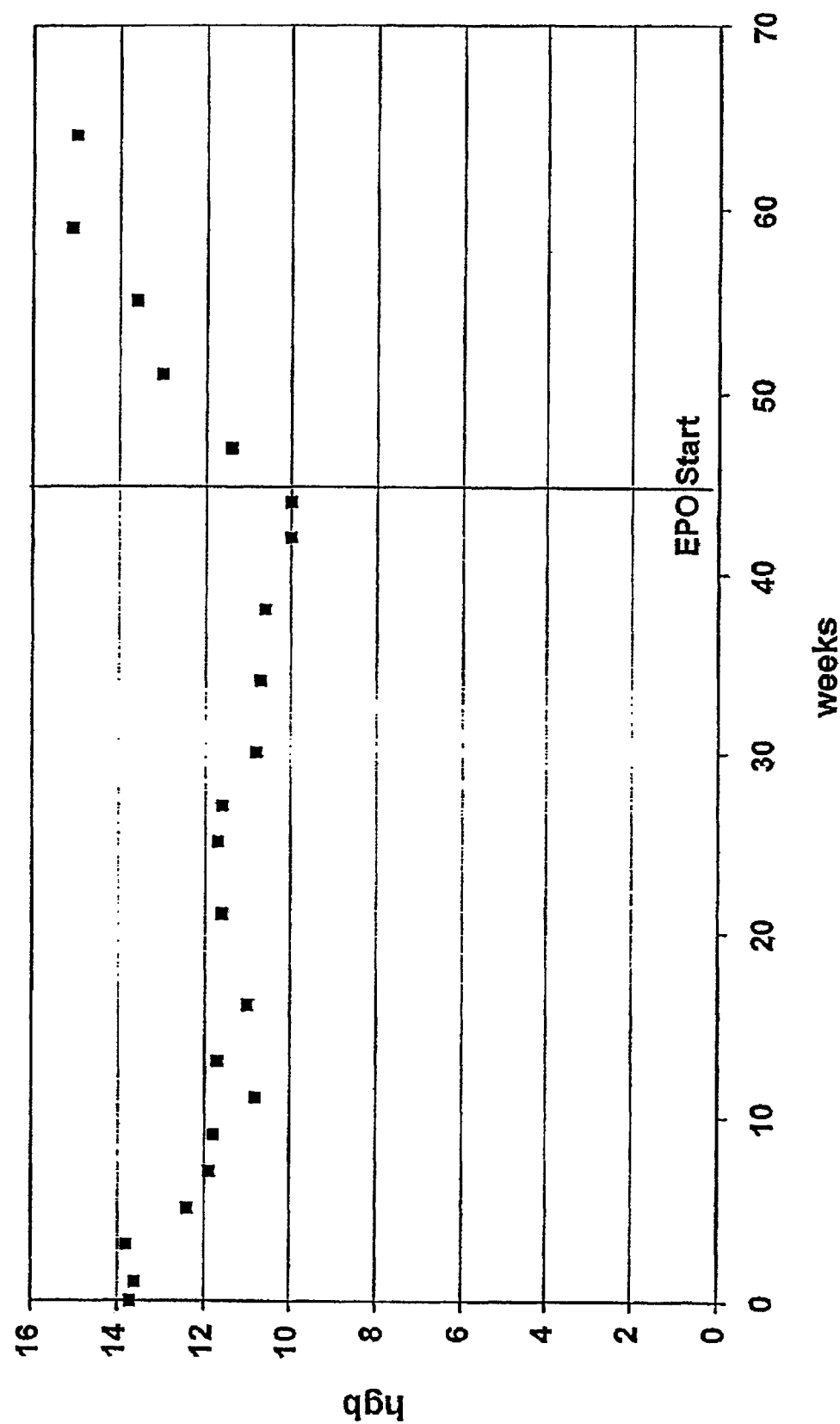
Figure 2.17

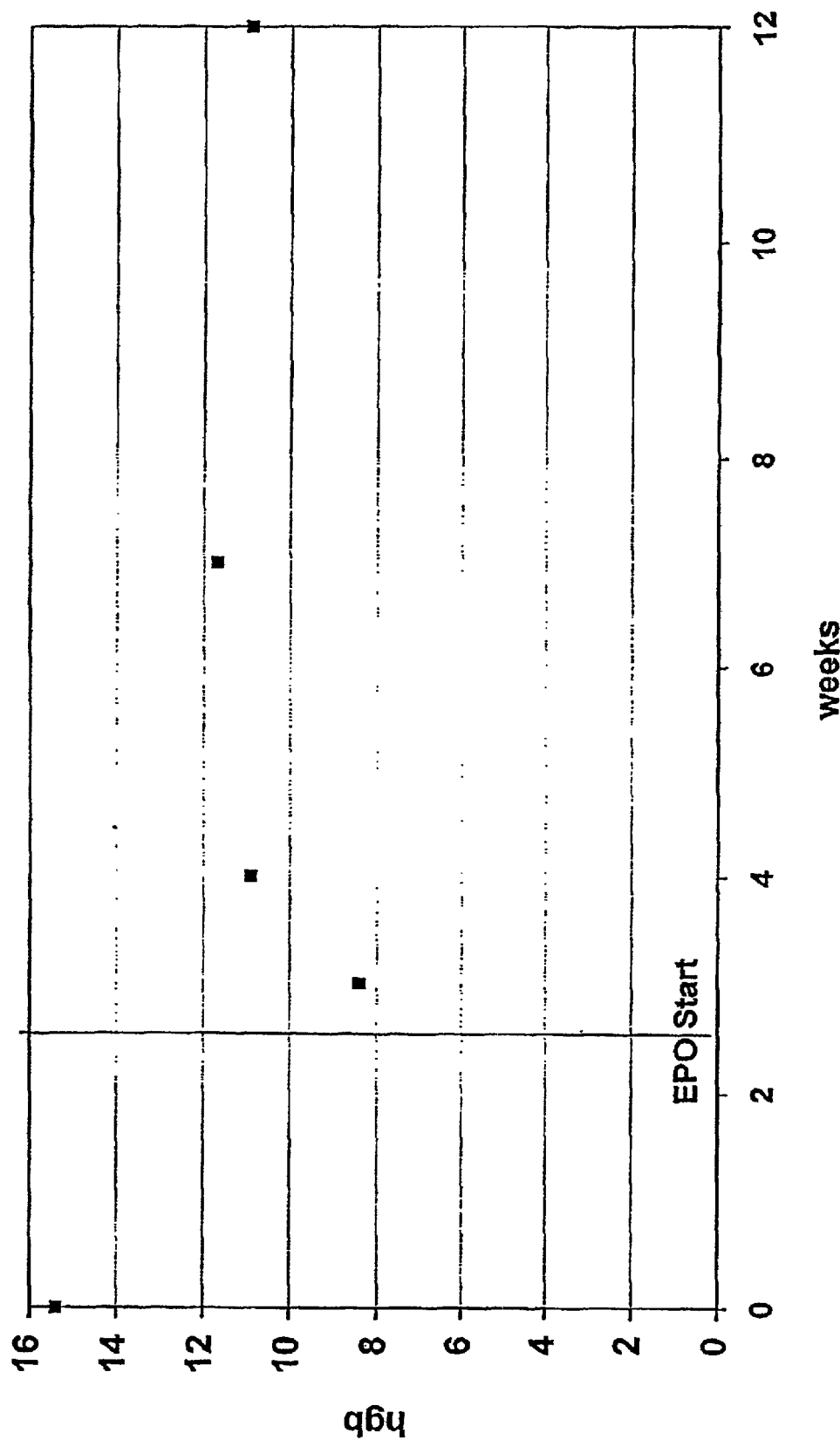
Figure 2.18

METHOD OF TREATING ANEMIA CAUSED BY RIBAVIRIN TREATMENT OF HEPATITIS C USING ERYTHROPOIETIN ALPHA

FIELD OF THE INVENTION

The present invention is directed to a new use for Erythropoetin ("EPO"), such as EPO alpha, for treating hepatitis C and/or anemia caused by hepatitis C treatment. Accordingly, the invention involves using EPO with hepatitis C treatment, such as Ribavirin ("RBV") and/or interferon such as alpha-interferon ("α-IFN" or "IFN"); and thus, the invention pertains to methods involving administration of EPO, RBV and α-IFN, or EPO and RBV, and compositions Various documents are cited herein, e.g., in the text and/or in a reference section. There is no admission that any of the various documents cited in this text are prior art as to the present invention. Any document having as an author or inventor person or persons named as an inventor herein is a document that is not by another as to the inventive entity herein. All documents cited in this text ("herein cited documents") and all documents cited or referenced in herein cited documents are hereby incorporated herein by reference. All specifications, manufacturer's data sheets, and the like for products referenced herein, and all documents cited therein, are hereby incorporated herein by reference.

BACKGROUND OF THE INVENTION

Erythropoietin ("EPO") is one of the red blood cell stimulating factors in the human body. Recombinant technology has made manufacture of this stimulating factor colony possible and its use in treating anemia caused by cancer chemotherapy, acquired immune deficiency syndrome ("AIDS") and renal failure. The recombinant product has been shown to be biologically identical to human erythropoietin.

A normal response to anemia in humans is the release of EPO and a corresponding rise in the hemoglobin level. There can be either an inadequate production of EPO or a lack of response to EPO by the bone marrow. When ribavirin is administered by itself, it gets pumped into red blood cells and, once inside, gets phosphorylated. After it is phosphorylated, the ribavirin cannot get out of the red blood cell and its concentration builds up until the red blood cell bursts (hemolysis). This anemia can be severe and even life threatening, particularly in people with heart disease. The normal response to a hemolytic anemia is the release of EPO which stimulates the bone marrow to produce more red blood cells, and immature red blood cells (reticulocytes) will be discovered in the peripheral blood smear. When interferon is administered with ribavirin, however, it blocks the normal response of the bone marrow to respond to the anemia and the reticulocyte response is blunted. Administration of exogenous EPO such as Epoetin alpha can overcome this response and cause the bone marrow to produce more red blood cells, overcoming the inhibitory effect of the interferon.

Recently, great importance has been placed on using ribavirin to eradicate hepatitis C. Hepatitis C, according to the Centers for Disease Control ("CDC"), afflicts over 3.9 million people in the United States today. Cirrhosis and liver failure caused by hepatitis C are the leading causes of liver transplant in the U.S. today. It is also an important global problem with as many as 50 million people afflicted with hepatitis C worldwide. The combination of interferon and ribavirin has been an approved treatment for hepatitis C since 1998. The addition of ribavirin has more than doubled the effect of the treatment to the hepatitis C virus. Clinical data from recent licensing trials shows that patients who receive at least 10.6 mg/kg of ribavirin have a sustained virologic response rate of over 40%, whereas those receiving less than that amount have a SVR (response) rate of only 28%. The maximum benefit is gained from a dose of ribavirin that is about 13 mg/kg. Such high doses of ribavirin cause a substantial increase of almost 50% in the incidence of anemia. The normal management of this would be to reduce the ribavirin dose and thereby reduce the efficacy of the interferon/ribavirin combination therapy. However, this would defeat the purpose of the hepatitis C treatment.

With respect to treating anemia caused by hepatitis C treatment in conjunction with ribavirin, reference is made to the following:

Albrecht, U.S. Pat. No. 6,172,046 B1, relates to a method of treating a patient having chronic hepatitis C infection. To eradicate detectable hepatitis C virus RNA, a combination therapy using a therapeutically effective amount of ribavirin and a therapeutically effective amount of interferon-alpha for a time period of from 20 up to 80 weeks is disclosed.

Draper, U.S. Pat. No. 5,610,054, relates to an enzymatic RNA molecule which cleaves RNA of the hepatitis C virus. Draper, U.S. Pat. No. 5,869,253, relates to an enzymatic RNA molecule which cleaves RNA encoding hepatitis C virus ("HCV") RNA, wherein the enzymatic RNA molecule comprises a substrate binding site and a nucleotide sequence within or surrounding the substrate binding site wherein the nucleotide sequence imparts to the enzymatic RNA molecule activity for the cleavage of the HCV RNA. Draper, U.S. Pat. No. 6,132,966, relates to an enzymatic nucleic acid molecule which inhibits hepatitis C virus replication.

Ise et al., U.S. Pat. No. 5,399,551, relates to an enhancer for antianemia effect of erythropoietin using a spherical carbon as an active ingredient in an amount effective for treating anemia in combination with erythropoietin. The enhancer is orally administered. The antianemia effect of erythropoietin can be enhanced, the dosage of erythropoietin can be decreased, and side effects from erythropoietin can be reduced. The invention further discloses a method of augmenting the anti-anemia effect of Erythropoetin by administering to a patient an effective amount of a spherical carbon in combination with a portion of an effective amount of Erythropoetin for treating anemia.

*Population Pharmacokinetic and Pharmacodynamic Analysis of Ribavirin in Patients with Chronic Hepatitis C*, by J. Frank Jen, Paul Glue, Samir Gupta, Demetrius Zambas and Gerald Hajian (Therapeutic Drug Monitoring, Vol. 22, No. 3, 2000) ("Population"), reported that "Athough anemia is a well-established adverse effect of ribavirin therapy, the association between drug concentrations and extent of anemia has not been thoroughly investigated. Earlier reports (22, 23) found that greater mean falls in hemoglobin were associated with higher daily ribavirin doses.

Despite the mean trends the variability of these data was high, suggesting that it would not be possible to establish a concentration range below which hemolysis would not occur, or above which anemia was inevitable. From a practical perspective, the most appropriate method of dealing with treatment related anemia would appear to be through dose reduction of ribavirin, although this analysis indicates that this should be based on individual hemotologic responses to ribavirin rather than based on serum ribavirin concentrations."

Thus, there is teaching in the art to reduce RBV—reduce the HCV treatment—to address anemia. Teachings such as this teach away from addressing anemia by other means and therefore teach away from the present invention.

Poduslo et al., U.S. Pat. No. 5,604,198, relates to a method of enhancing an ability of a neurologically active compound to penetrate the blood nerve barrier ("BNB") or blood brain barrier ("BBB"), by administering a conjugate comprising the neurologically active compound linked to a carrier molecule that has been shown to have a substantial permeability coefficient across the BNB and BBB. Poduslo et al., U.S. Pat. No. 5,670,477, relates to a method of enhancing the ability of a neurologically active compound to penetrate the blood nerve barrier ("BNB") or blood brain barrier ("BBB") comprising parenterally administering to a mammal in need of treatment with the neurologically active compound, a conjugate consisting of an effective amount of the neurologically active compound linked to a polyamine having a substantial permeability coefficient across the BNB or BBB.

Strickland, U.S. Pat. No. 5,661,125, relates to stable compositions of erythropoietin that contain an antimicrobial preservative thereby providing a multi-dose formulation. Preservatives useful in the pharmaceutical compositions of the invention include benzyl alcohol, parabens, phenol and mixtures thereof. Other additives, including buffers, may be included in the composition.

Tam, U.S. Pat. No. 6,063,772, relates to administering ribavirin to a patient in a dosage range which is effective to modulate lymphokine expression in activated T cells. In particular, ribavirin is used to suppress Th2-mediated T cell responses and promote Th1-mediated T cell response. Instead of administering ribavirin in its well-recognized role as an anti-viral agent, ribavirin is thus used in the treatment of imbalances in lymphokine expression. Such imbalances may be found to be concomitants of allergic atopic disorders, such as allergic asthma and atopic dermatitis, helminthes infection and leishmaniasis, and various primary and secondary immunodeficiencies, which may or may not also be associated with viral infection.

*Interferon (IFN) and Ribavirin (RBV) Therapy for Hepatitis C (HCV) in HIV-Coinfected Patients, 12 Month Follow-Up, 7th Conference on Retroviruses and Opportunistic Infections*, at the Birth of a Century, Research Toward Ending AIDS, Program and Abstracts, Jan. 30–Feb. 2, 2000, by K. Weisz, D. Goldman, A. Talal, M. Malicdem and D. Dieterich, reported that (1) IFN alone does not adversely affect HIV RNA, and can have little effect on HCV RNA; (2) IFN and RBV have little effect on HIV RNA clinically, and have a sizeable effect on HCV RNA; (3) anemia, a side effect of RBV, can be successfully treated with erythropoietin. However, this study fails to teach or suggest the present invention as it did not involve co-administered or concomitant administration as herein; and, because the study concerned and HIV positive patients, not HCV patients who are HIV negative or immunocompetent, as there is a prejudice in the art against employing EPO in immunocompetent individuals because EPO administration can give rise to anti-EPO antibodies. (However, methods, kits and compositions of the invention are not necessarily excluded from being employed with respect to immunocompromised individuals.)

Yatvin et al., U.S. Pat. No. 5,543,390, relates to a method and a reagent for delivering biologically active compounds to phagocytic mammalian cells. The patent also relates to an uptake of such biologically active compounds by phagocytic cells and delivery of such compounds to specific sites intracellularly. The invention more particularly relates to methods of facilitating the entry of antimicrobial drugs and other agents into phagocytic cells and for targeting such compounds to specific organelles within the cell. The '390 patent further relates to compositions of matter and pharmaceutical embodiments of such compositions comprising conjugates of such antimicrobial drugs and agents covalently linked to particulate carriers generally termed microparticles. In particular embodiments, the antimicrobial drug is covalently linked to a microparticle via an organic linker molecule which is the target of a microorganism-specific protein having enzymatic activity. The 390 patent also provides cell targeting of drugs wherein the targeted drug is only released in cells infected with a particular microorganism. Alternative embodiments of such specific drug delivery compositions also contain polar lipid carrier molecules effective in achieving intracellular organelle targeting in infected phagocytic mammalian cells. Particular embodiments of such conjugates comprise antimicrobial drugs covalently linked both to a microparticle via an organic linker molecule and to a polar lipid compound, to facilitate targeting of such drugs to particular subcellular organelles within the cell. Also provided are porous microparticles impregnated with antimicrobial drugs and agents wherein the surface or outside extent of the microparticle is covered with a degradable coating that is specifically degraded within an infected phagocytic mammalian cell. Methods of inhibiting, attenuating, arresting, combating and overcoming microbial infection of phagocytic mammalian cells in vivo and in vitro are also provided. While technology in the 390 patent may be useful in the practice of the herein invention, the 390 patent fails to teach or suggest the present invention.

Yatvin et al., U.S. Pat. No. 5,543,391, relates to a composition having a biologically-active compound that is an antimicrobial drug, a porous microparticle, and an organic coating material, wherein the biologically-active compound is impregnated within the porous microparticle, and the microparticle is coated with the organic coating moiety, and wherein the organic coating material comprises a compound that is specifically degraded inside a phagocytic mammalian cell infected with a microorganism to allow release of the biologically-active compound within the infected cell.

Foregoing patents and/or other background information discussed may involve either an EPO composition or an EPO enhancer. However, none of the patents foregoing patents and/or background information discloses or suggests using EPO as an anti-anemia treatment in conjunction with the ribavirin-interferon-alpha treatment for HIV negative or immunocompetent hepatitis C patients and/or in a co-administration regimen and/or via a kit, as herein.

And, in this regard, it is again mentioned that administration of EPO can give rise to anti-EPO antibodies, inter alia, such that there may be a prejudice against administration of EPO to immuno-competent (e.g., HIV negative) individuals.

Thus, it is believed that heretofore the present invention has not been taught or suggested.

SUMMARY OF THE INVENTION

It is an object of the present invention to provide a new use of Erythropoetin ("EPO") to treat an anti-anemia condition caused by the combination treatment of ribavirin and interferon-alpha. It is another object of the present invention to provide a method of administering EPO to patients with ribavirin-induced anemia to counteract a hemolytic effect and to allow patients to take the maximum effective dosage of ribavirin and interferon-alpha necessary to eradicate hepatitis C.

It is and has been surprisingly found that EPO works the same in both HIV positive and HIV negative patients with HCV.

In this text, the term "comprising", "comprise", "comprises" and other forms of "comprise" can have the meaning described to these terms in U.S. Patent Law and can mean "including", "include", "includes" and other forms of "include".

Co-administering is administration at the same time or at about the same time, i.e., via a composition or kit containing all of EPO, interferon-alpha and ribavirin; for instance, co-administering can involve a sequential administration of RBV, EPO and IFN e.g., via a visit to a healthcare provider, or via patient self administration.

More in particular, RBV typically is provided and administered in solid, e.g., capsule or tablet form or in the form of an inhaler, with the tablet or capsule being usually employed with respect to HCV. Patients usually take 2 to 3 tablets or capsules of RBV/day (e.g., Rebetol, such as 800 or 1000–1200 mg/daily). IFN is provided in an injectable form, as is EPO. For instance, Intron A (IFN) injection in a 3 MIU dose can be administered three times weekly; and PEG-IntronNT (pegylated IFN) injection in a 0.5 or 1.5 mcg/kg dose can be administered once weekly (QW). Combinations of RBV and IFN can include: PEG-IntronNT injection 1.5 mcg/kg once weekly (QW) plus Rebetol capsules 800 mg/daily for 48 weeks (PEG 1.5/R); PEG-Intron 1.5 mcg/kg QW plus Rebetol 1000–1200 mg/daily for four weeks followed by PEG-Intron 0.5 mcg/kg QW plus Rebetol 1000–1200 mg/daily for 44 weeks (Peg 0.5/R); or Intron A injection 3 MIU/three times weekly plus Rebetol Capsules 1000–1200 mg/daily for 48 weeks (Rebetron). Patients can self-administer EPO, RBV and IFN.

The invention envisages kits that contain EPO, RBV and IFN, such that the patient can administer the EPO, RBV and IFN; e.g., RBV orally twice daily (e.g. once in morning, once in evening or three times daily including a morning dose), IFN once weekly or three times weekly via injection, and EPO at least once weekly via injection. The patient can therefore obtain a one-week, two-week, three-week, monthly, bimonthly, three-month, four-month, five-month, six-month, seven-month, eight-month, nine-month, ten-month, eleven-month, or annual supply of EPO, RBV and IFN, via a kit of the invention.

The kit thus advantageously contains EPO e.g., for injection, IFN e.g., for injection, suitable devices for administration via injection (e.g., syringes) if components are supplied for administration via injection, RBV e.g., tablets or capsules, and optionally (but advantageously) instructions for administration/use. The patient can therefore each day self-administer or be administered the RBV (e.g., orally), advantageously with a first dose in the morning or upon awakening. On selected day or day(s), such as in the morning or upon awakening, with the first dose of RBV, the patient can then also administer IFN. And, on selected day or day(s), such as in the morning or upon awakening, also with a first dose of RBV, the patient can additionally administer the EPO.

Thus, the patient can be having a co-administration of EPO and RBV.

Moreover, at least once weekly, the patient can be having co-administration of RBV, IFN and EPO, advantageously at the same time, e.g., via oral administration of RBV and sequential injections of IFN and EPO.

The patient self administrations can, of course, be performed by a healthcare provider.

Even more advantageous, the EPO and IFN can be provided for admixture and/or in an admixed state, so that the EPO and IFN administration is via one injection of a combination of EPO and IFN. Thus, when the EPO and IFN are to be co-administered, it may be possible to admix them for a single injection containing both. However, an injection for each of the EPO and IFN and oral administration of RBV are presently preferred.

A preferred embodiment involves a kit containing EPO for once weekly administration by injection, IFN for once weekly administration by injection, and RBV for twice daily oral administration. The kit can contain instructions for administration. The kit can also contain devices for administration via injection. Again, the kit can contain an "N" week, wherein "N" is an integer advantageously from 1–52 (e.g., one week, or two week, or three week, or four week, or five week, or six week, or seven week, or eight week, or nine week, or ten week, or eleven week, or 12 week or 13 week or 14 week etc. up to 52 week) supply of EPO, IFN and RBV.

Accordingly, the invention provides methods for administering RBV and EPO or RBV, EPO and IFN for treatment of HCV and/or anemia caused by HCV, as well as compositions containing EPO and IFN, and kits containing RBV and EPO, or, RBV, EPO and IFN, with such kits optionally containing instructions for administration and/or devices for administration, and the EPO and IFN, if together in the kit, can be in forms so that when co-administered they can be admixed prior thereto and/or they are in an admixed form for co-administration.

In instances where the HCV can be treated by RBV without IFN, embodiments can involve the foregoing, with the IFN omitted.

The invention further comprehends methods for co-administering RBV and EPO or RBV, EPO and IFN, as well as compositions containing EPO and IFN, or RBV and EPO, or RBV, IFN and EPO.

These and other objects and embodiments of the invention are provided in, or are obvious from, the following detailed description of the invention.

BRIEF DESCRIPTION OF THE DRAWING(S)

Figure 1:
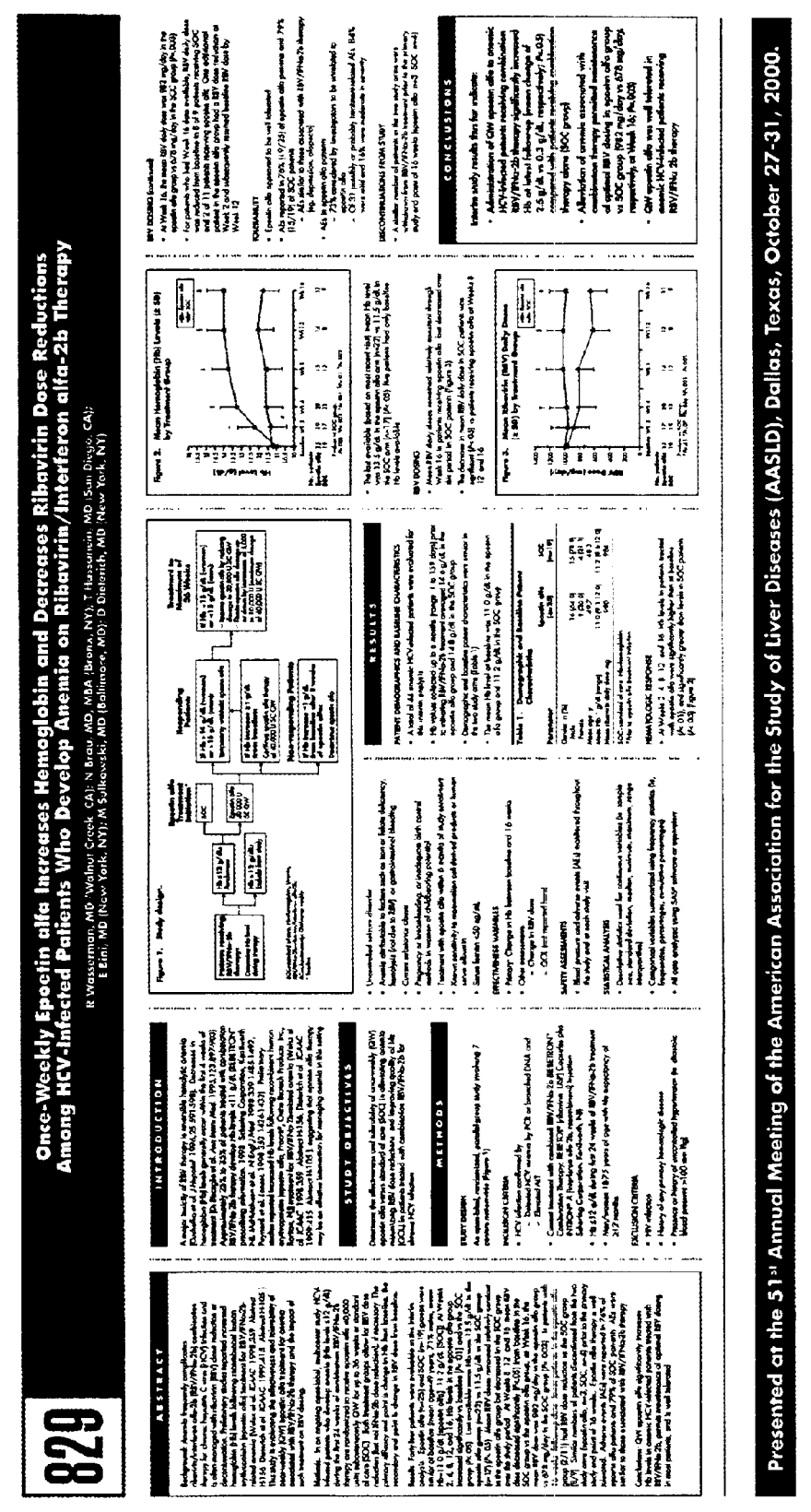

FIG. 1 shows a study design and results thereof for administering EPO with RBV and/or IFN-α.

Figures 2, 3, 4, 5, 6, 7, 8, 9, 10, 11:
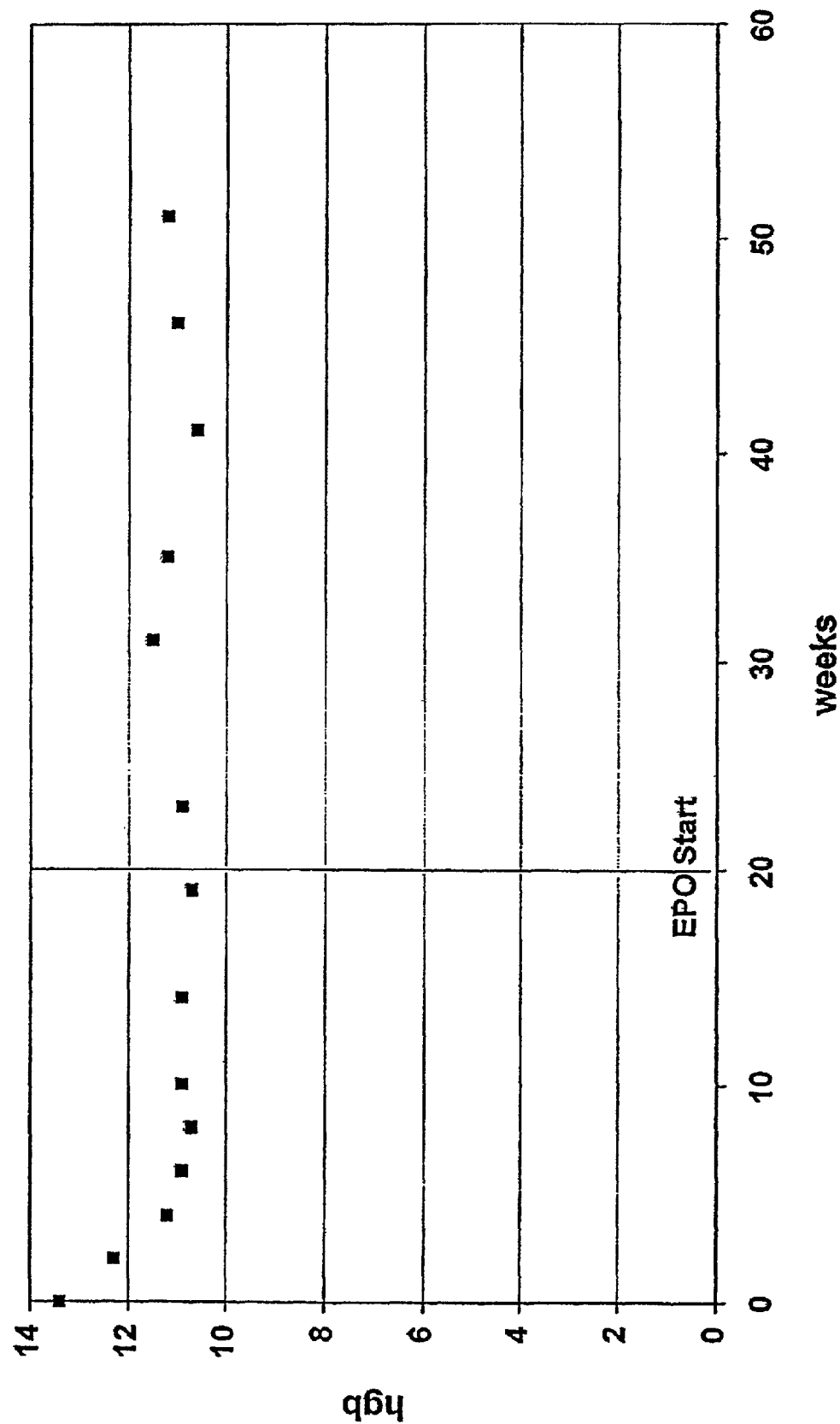
FIG. 2 shows a collection of plots of hemoglobin levels by time for 18 EPO-treated patients.

FIG. 2.1 represents Subject #2;
FIG. 2.2 represents Subject #3;
FIG. 2.3 represents Subject #4;
FIG. 2.4 represents Subject #5;
FIG. 2.5 represents Subject #6;
FIG. 2.6 represents Subject #7;
FIG. 2.7 represents Subject #8;
FIG. 2.8 represents Subject #11;
FIG. 2.9 represents Subject #13;
FIG. 2.10 represents Subject #14;
FIG. 2.11 represents Subject #15;
FIG. 2.12 represents Subject #16;
FIG. 2.13 represents Subject #18;
FIG. 2.14 represents Subject #19;
FIG. 2.15 represents Subject #20;
FIG. 2.16 represents Subject #21;
FIG. 2.17 represents Subject #22; and
FIG. 2.18 represents Subject #23.

DETAILED DESCRIPTION OF THE INVENTION

The present invention claims and discloses a new use for erythropoietin in treating ribavirin-interferon-alpha induced anemia. The present invention can be administered to humans as well as animals infected with Hepatitis C virus or HIV or HIV and HCV or who are suffering from anemia. The Erythropoetin can be administered in a liquid preparation and/or administered as a vector for in vivo expression. Specifically, the present invention also evaluates the clinical benefit of erythropoietin in ribavirin/interferon-induced anemia.

The combination of ribavirin (RBV) and interferon-alpha (IFN-α) is standard treatment for hepatitis C (HCV)-infected patients. Anemia (hemoglobin <10 g/dl), severe enough to warrant dose reductions or cessation of therapy, occurs in up to 10% of individuals prescribed these medications, but a drop in hemoglobin of >3 grams/dl occurs in 54% of people treated with RBV and IFN-α.

Nearly four million individuals in the United States, approximately two percent of the population, are infected with the hepatitis C virus. Of the 30,000 acute cases annually, as many as 85% will progress to chronic infection. With 8,000 to 10,000 deaths each year attributed to HCV in the U.S., the infection has become the primary indication for hepatic transplantation. In HIV seropositive patients, as many as 40% of the nearly 1 million HIV seropositive patients have HCV.

Biochemical (normalization of alanine aminotransferase), virologic (loss of serum HCV RNA), and histologic (improvement in hepatic histology) indicators are used to determine a response to therapy for HCV.

Monotherapy with IFN-α3 million units three times per week (TIW) results in a biochemical end-of-treatment response in 35 to 50% of subjects and a sustained response in 10 to 35% of subjects. Recently the combination of IFN-α and RBV, a synthetic nucleoside analog with antiviral activity, was approved by the U.S. Food and Drug Administration for the treatment of HCV. The sustained response rate is more than twice as high among subjects treated with the combination of IFN-α/RBV than among those treated with IFN-α alone.

Anemia is a major side effect of IFN-α/RBV combined therapy, necessitating dosage reduction in more than 10% of treated individuals. Although the primary mechanism of anemia in patients who receive the combination of IFN-α and RBV is thought to be hemolysis, other mechanisms, such as the down-regulation of the erythropoietin receptor, may contribute. In response to hypoxia, erythropoietin stimulates the production, maturation, and release of erythrocytes from the bone marrow. In cases of endogenous erythropoietin deficiency or an inadequate hypoxic response, recombinant human erythropoietin (r-HuEPO, Epoetin alpha) improves anemia associated with HIV-infection, chronic diseases, and malignancies. Similarly, anemia induced by several medications including zidovudine, a synthetic nucleoside analog similar to RBV, is improved by Epoetin alpha. Therefore, the present invention evaluated the benefit of Epoetin alpha in HCV-infected individuals who became anemic after the initiation of the IFN-α/RBV combined treatment.

The combination of IFN-α/RBV for the treatment of HCV infection more than doubles the sustained response rate when compared to IFN-α monotherapy. Anemia, however, is a dose-limiting side effect of the combination therapy in a significant patient population, e.g., more than 10% of individuals who receive the medications. The inventor of the present invention has shown that Epoetin alpha increases hemoglobin levels in HCV-infected patients who become anemic after IFN-α/RBV therapy to a level equivalent to that of patients who do not develop anemia.

Hepatitis C is the newest opportunistic infection in HIV patients as declared by the U.S. Public Health Service in 1999. It progresses to cirrhosis and death much more rapidly in patients with HIV and is the leading cause of death in many HIV clinics. Since the era of highly active antiretroviral therapy began in 1995, HIV patients are living longer and suffering more ill effects of their hepatitis C infection. It has become vital therefore to treat hepatitis C in patients with HIV. One of the early complications of HIV and its treatment was anemia. Erythropoietin has been used to successfully treat HIV-related anemia. Indeed, anemia in HIV patients has been shown to have a negative effect on survival. Thus, many physicians were reluctant to use interferon and ribavirin in HIV-infected patients because of their fear of anemia and because of concern about ribavirin inhibiting HIV medication.

Although anemia associated with IFN-α/RBV therapy for HCV infection is usually attributed to hemolysis, other mechanisms, such as anemia of chronic disease (ACD), may contribute. ACD is common in patients with infectious, inflammatory, and neoplastic disorders, and it is thought to result from three processes: a moderate shortening of erythrocytes survival, an inability of the bone marrow to respond to the resulting demand for increased erythrocyte production, and the impaired mobilization of iron stores in the reticuloendothelial system.

Reduced responsiveness of the bone marrow to erythropoietin has been described in association with malignancy, rheumatoid arthritis, and HIV infection. In the setting of a demand for increased erythrocyte production, the impaired ability of the bone marrow to respond to erythropoietin results in reduced erythrocyte production and anemia. Several proinflammatory cytokines, including tumor necrosis factor-α (TNF-α, interleukin-1a (IL-1a), interleukin-6 (IL-6), and interferon-γ (IFN-γ), have been associated with ACD and a down-regulation in endogenous erythropoietin levels. Chronic infection with HCV is associated with an increase in proinflammatory cytokines particularly IFN-γ, TNF-α, and IL-2. Intrahepatic proinflammatory cytokine mRNA is increased in HCV-infected individuals compared to uninfected controls and further increases are associated with worsening hepatic injury.

The association between proinflammatory cytokines and ACD and the increase in proinflammatory cytokines observed in HCV-infected individuals raises the possibility that these cytokines may contribute to reduced bone marrow responsiveness to erythropoietin. The results of this study raise the possibility that two separate processes may underlie the hemoglobin reduction in HCV-infected individuals who develop anemia after initiation of IFN-α/RBV treatment, a hemolytic component and a biochemical component. RBV may result in an increase in erythrocyte hemolysis while an increase in proinflammatory cytokines may result in decreased responsiveness of the bone marrow to erythropoietin. Furthermore, the reduced bone marrow responsiveness to erythropoietin may only become apparent after the onset of erythrocyte hemolysis secondary to IFN-α/RBV.

Epoetin alpha significantly increases hemoglobin levels in several disorders characterized by decreased bone marrow responsiveness to erythropoietin, including rheumatoid arthritis, cancer, and HIV infection. Epoetin alpha increases the number of reticulocytes released from the bone marrow into the circulation and reduces apoptosis among late erythroid precursors, thereby increasing hemoglobin levels. It may also compensate for the inhibitory effect of proinflammatory cytokines on erythropoiesis and, thus, may be an efficacious therapy for IFN-α/RBV-associated anemia in HCV-infected individuals.

Both IFN-α and RBV are capable of directly inhibiting erythropoiesis through mechanisms that are known to be sensitive to the action of Epoetin alpha. For example, interferons reduce the growth rate of normal hematopoietic cells, thereby inhibiting the proliferation of erythroid progenitor cells. In addition, IFN-α diminishes erythropoietin production in hepatocyte cultures. RBV is a synthetic nucleoside analog similar to zidovudine, a drug shown to cause a concentration-dependent down-regulation of the erythropoietin receptor. When administered to HIV-infected individuals to treat zidovudine-associated anemia, Epoetin alpha may compensate for erythropoietin receptor down-regulation, thereby reversing the anemia.

In 13 out of the 18 individuals who received Epoetin alpha, the dose of RBV was also reduced. Eight subjects had the RBV dose reduced prior to an initiation of Epoetin alpha. The RBV dose reduction may have partially corrected the anemia (possibly through a decrease in hemolysis) while exogenous erythropoietin may have been required to overcome the reduced responsiveness of the bone marrow to Erythropoetin.

The administration of Epoetin alpha in IFN-α/RBV treated, HCV-infected individuals with profound decreases in hemoglobin provides important clinical benefits by reversing the anemia, relieving anemia-associated symptoms such as fatigue and dyspnea, and improving an individual's ability to tolerate the full course of antiviral therapy at efficacious dosages.

The present invention directs to an administering of EPO, e.g., a specific predetermined amount of EPO, such as in a liquid preparation and/or as a vector in a liquid, to patients on a weekly basis. The liquid preparation can contain EPO as disclosed in U.S. Pat. Nos. 5,955,422; 5,756,349; 5621,080; 5,618,698; 5,547,933; 4,703,008; 5,856,298; 5,661,125; 5,106,760; 4,703,008; 5,856,298; 5,661,125; 5,106,760; 4,558,006; 5,574,018; 5,354,934; 5,013,718; and 4,667,016. Alternatively, EPO can be administered as a vector that expresses the EPO in vivo, and this can reduce the frequency of the injection. For example, EPO can be administered as a vector, as a plasmid vector, or as a virus vector, such as a DNA virus or a retrovirus that expresses the EPO.

Compositions of the present invention can include liquid preparations for orifice, e.g., oral, nasal, anal, vaginal, peroral, intragastric, mucosal (e.g., perlingual, alveolar, gingival, olfactory or respiratory mucosa), etc.; administration such as suspensions, syrups or elixirs; and preparation for parenteral, subcutaneous, intradermal, intramuscular or intravenous administration (e.g., injectable administration), such as sterile suspensions or emulsions. Such compositions may be in admixture with a suitable carrier, diluent, or axcipient, such as sterile water, physiological saline, glucose or the like. The compositions can also be lyophilized. The compositions can contain auxiliary substances, such as wetting or emulsifying agents, pH buffer agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17$^{th}$ Edition, 1985, incorporated herein by reference, may be consulted to prepare suitable preparations, without undue experimentation.

EPO is commonly administered when the hemoglobin level falls to a level of 10 or 15 grams/dl. When EPO is administered to a patient subcutaneously, it is given at a dose of about 40,000 units per week. If an inadequate response is seen, the dose can be increased to about 60,000 units, or lowered to about 20,000 units on a weekly basis depending on the response generated in a patient. EPO treatment for the IFN-α/RBV induced anemia is used as long as is necessary during IFN-α/RBV combined treatment, which is usually about 12 months for genotype 1, and may be about 6 months for hepatitis C genotype 2 or 3.

The invention will now be further described by the following non-limiting Examples, provided for illustration.

EXAMPLES

Example 1

In an open-label, prospective pilot study, 56 subjects with chronic HCV infection were treated with both RBV and IFN-α. Eighteen subjects with anemia (hemoglobin <10 g/dl or decreased ≧1 g/dl) and reduced exercise tolerance following IFN-α/RBV initiation were treated with Epoetin alpha (up to 40,000 units per week subcutaneously). Remaining nonanemic subjects (38/56) who did not receive Epoetin alpha served as a control group. The two groups were followed for means of 25.3 and 21.2 weeks, respectively. At baseline, mean hemoglobin levels were not significantly different in the subjects who received epoetin alpha compared to those who did not receive the medication (14.3 g/dl vs. 15.1 g/dL, n.s.). At the time of epoetin alpha initiation, the mean hemoglobin level declined 25.4% (to 10.6 g/dL) in the group receiving this treatment. At the last study visit, mean hemoglobin levels were 12.7 g/dL among patients receiving epoetin alpha vs. 13.0 g/dL among controls (difference n.s.) reflecting a recovery of 65.5% in mean hemoglobin level in the epoetin alpha treated group. Two thirds of subjects receiving epoetin alpha reported improved symptoms. This pilot study suggests that epoetin alpha increases hemoglobin levels and improves dyspnea in subjects who develop anemia after initiation of IFN-α and RBV.

Example 2

A study of interferon alone and interferon plus ribavirin for hepatitis C in HIV-infected patients was performed. Ten patients received interferon alone and 11 received the combination treatment of interferon alpha and ribavirin. Median liver biopsy fibrosis score for both groups was 2.1. In the interferon alone group, at 3 months, there was no change in HCV RNA, CD4 dropped from a median of 190 to 186 cells/ml and HIV RNA dropped from a median of 1500 copies per ml to less than 400. At the same time point, 3 months, in the combination group, the HCV RNA dropped from 3.2 million to less than about 600 copies/ml. CD4 cells dropped from a median of 544 to 237, but percentage CD4 cells did not change. The main adverse event was anemia which occurred in 5/21(23.8%). This was treated with erythropoietin 40,000 units weekly when the hemoglobin declined to to 10 g/dl. This treatment resulted in a rise in hemoglobin to 12.7 g/dl after a median of 4 weeks treatment. This was the first report of this treatment in patients with HIV infection as well as hepatitis C.

Subsequently 40,000 units of Erythropoetin alpha was used on a weekly basis in patients with hemoglogin level of 11 gr/dl or less as a result of ribavirin-induced anemia. This was done in both HIV seronegative individuals and HIV seropositive individuals. This has resulted in a substantial increase in their quality of life as well as an increase in the amount of ribavirin that they have been able to take.

Example 3

Fifty-six chronically HCV-infected (≧90 days) subjects who were treated with IFN-α (3 million units TIW) and RBV (1000 mg/d for subjects <75 kg or 1200 mg/d for subjects ≧75 kg) were entered into an open-label, pilot, prospective study at several centers. Subjects were excluded if they were infected with the human immunodeficiency virus type-1 or had a history of anemia, chronic renal disease, or coronary artery disease. RBV doses were adjusted by treating physicians as clinically indicated throughout the study.

Following INF-α/RBV initiation, subjects with new-onset anemia (hemoglobin ≦10 g/dL or ≧2 g/dL decrease in hemoglobin) or a decrease in hemoglobin accompanied by decreased exercise tolerance (providers' impressions) received epoetin alpha (up to 40,000 units per week, subcutaneously). Subjects who did not become anemic and who did not receive epoetin alpha served as a control group.

After initiation of epoetin alpha therapy, subjects were evaluated at a 2-week interval for 8 weeks and every 4 weeks thereafter for a maximum of 40 weeks. At each visit, laboratory safety parameters were obtained and, for most subjects, health-care providers recorded whether improvement had occurred in symptoms that typically occur as a side-effect of anemia or after therapy with IFN-α/RBV (e.g., flu-like symptoms, fatigue, dyspnea).

Hemoglobin levels were compared at baseline (prior to IFN-α/RBV initiation) and at the last visit (IFN-α/RBV discontinuation visit) between subjects who received epoetin alpha and those who did not. In addition, clinical benefit of epoetin alpha therapy was evaluated by comparing the percent decline in hemoglobin levels from baseline to initiation of epoetin alpha with the percent recovery in these levels by the last visit.

Fisher's exact test or the t-test was used to evaluate the significance of differences between groups with respect to demographic characteristics. The t-test was used to compare mean hemoglobin levels between individuals who received epoetin alpha and those who did not.

After a mean of 15.9±11.5 weeks (range: 3–44 weeks) following IFN-α/RBV treatment initiation, 18 subjects (32.1%) who developed new-onset anemia and reduced exercise tolerance were treated with epoetin alpha (up to 40,000 units per week, subcutaneously). The comparison group comprised 38 subjects (67.9%) who did not develop anemia and who did not receive epoetin alpha.

Subjects in the group that received epoetin alpha and those in the control group were similar with respect to age, the dose of RBV that was prescribed, HCV genotype, and baseline hemoglobin (14.3±1.4 g/dL vs. 15.1±1.4 g/dL, respectively; n.s.) (Table 1). Males were somewhat underrepresented in the subjects who received epoetin alpha. In the epoetin alpha group, RBV doses were lowered prior to the initiation of epoetin alpha therapy in eight subjects and at the time epoetin alpha was initiated in five additional subjects.

Subjects who received epoetin alpha were followed for a mean of 25.3±15.6 weeks (range: 14–40 weeks) while individuals who did not receive epoetin alpha were followed for a mean of 21.2±13.2 weeks (range: 2–47 weeks). The mean hemoglobin level in the subjects who received epoetin alpha decreased from baseline by 25.4±8.9 percent (from 14.3±1.4 g/dL to 10.6±1.0 g/dL). After initiation of epoetin alpha, hemoglobin increased by an average of 65.5±56.3 percent. At the last visit, mean hemoglobin levels were not significantly different in the two groups (12.7±1.7 g/dL in the epoetin alpha group vs. 13.1±1.4 g/dL in the comparison group; n.s.).

Among the 53 patients with complete data, the frequency and duration of symptoms were similar between the two groups with two exceptions (Table 2). Dyspnea was reported by significantly more subjects in the epoetin alpha group than in the group that did not receive epoetin alpha (80.0% vs. 23.6%, respectively, P<0.001). Likewise, the median duration of fatigue was significantly more prolonged among those in the epoetin alpha group in comparison to those in the other group (8.2 vs. 5.3 weeks, respectively, P<0.05).

Anecdotal reports by health care providers indicated that anemia-related symptoms improved in two-thirds of patients in the epoetin alpha group by the time of the last visit.

Table 3 shows a lab average for HCV/HIV patients on Interferon and RBV.

TABLE 1

PATIENT PROFILE

|  | Epoetin alpha (N = 18) | No epoetin alpha (N = 38) |
|---|---|---|
| Mean (±s.d.) age (yrs) | 47.7 (7.8) | 44.5 (7.4) |
| Male (%) | 38.9 | 68.4 |
| Mean (±s.d.) baseline hemoglobin (g/dL) | 14.3 (1.4) | 15.1 (1.4) |
| RBV dose (%): |  |  |
| 1000 mg/d | 72.2 | 84.2 |
| 1200 mg/d | 27.8 | 15.8 |
| HCV genotype (%)*: |  |  |
| 1a or 1b | 53.3 | 55.3 |
| Other | 33.3 | 23.7 |
| Untested | 13.3 | 21.0 |

*Missing data for three patients in the Epoetin alpha group.

TABLE 2

SUBJECTS' SYMPTOMS

|  | Epoetin alpha (N = 15) | No epoetin alpha (N = 38) |
|---|---|---|
| Dyspnea (%) | 80.0 | 23.6* |
| Median duration (wks) | 6.6 | 4.6 |
| Fatigue (%) | 73.3 | 60.5 |
| Median duration (wks) | 8.2 | 5.3† |
| Flu-like symptoms | 46.7 | 15.8 |
| Median duration (wks) | 2.7 | 5.4 |

*P < .001
†P < .05

TABLE 3

LAB AVERAGES FOR HCV/HIV PATIENTS ON INTERFERON AND RBA

| Initials | Testosterone | Triglycerides | Cholesterol | LDL | HDL | Glucose | ALT | AST | Total Protein | Ablumin | Epo | ANC | Hgb | WBC |
|---|---|---|---|---|---|---|---|---|---|---|---|---|---|---|
| RR | 1077.3 | 99.1 | 149 | 89.8 | 39.5 | 131.5 | 36.9 | 58.4 | 7.5 | 4 |  | 901.6 | 12.9 | 2.7 |
| AZ | 372.7 | 176.2 | 89 | 38.1 | 23.2 | 78 | 192.8 | 131.8 | 6.7 | 3.6 | 17.7 | 5793.3 | 12.1 | 6.8 |
| PB | 955.3 | 247.2 | 160.7 | 90.8 | 43.6 | 70 | 42.7 | 34.4 | 8.1 | 4.5 |  | 2562 | 12.2 | 4.3 |

TABLE 3-continued

LAB AVERAGES FOR HCV/HIV PATIENTS ON INTERFERON AND RBA

| Initials | Testosterone | Triglycerides | Cholesterol | LDL | HDL | Glucose | ALT | AST | Total Protein | Ablumin | Epo | ANC | Hgb | WBC |
|---|---|---|---|---|---|---|---|---|---|---|---|---|---|---|
| FK |  | 93.6 | 171.3 | 108 | 45 | 86.8 | 33.3 | 51.3 | 7.6 | 3.8 |  | 3057.7 | 10.9 | 6.2 |
| SSC | 544 | 145.5 | 129 | 75.8 | 24 | 95 | 86 | 60.1 | 7.6 | 4.4 |  |  |  |  |
| AC | 1140 | 149.5 | 184.5 | 116.5 | 38 | 103 | 37 | 22 | 7 | 4.6 |  |  |  |  |
| DT | 1461.3 | 260.7 | 258.7 | 108.6 | 47.4 | 86.5 | 93.3 | 71.5 | 8.3 | 4 | 10.6 | 888.6 | 14.2 | 4.7 |
| JC | 413 | 171.5 | 157 | 98 | 24.5 | 91.5 | 26.5 | 28 | 7.7 | 3.7 |  | 1773 | 14.7 | 3.4 |
| FG |  | 101 | 172 | 119 | 27.5 | 101 | 138.5 | 93.5 | 7.4 | 4.1 |  |  |  |  |
| RA | 583.6 | 168.6 | 121.8 | 75 | 25 | 104 | 52.2 | 37.3 | 6.8 | 4.3 |  | 2669.8 | 14.2 | 5.2 |
| RV | 209.8 | 247.8 | 238.8 | 161.4 | 27.7 | 71.6 | 54 | 50 | 8.3 | 4.2 | 59.2 | 2291.5 | 10 | 5.1 |
| RK | 590.8 | 135 | 207.6 | 135.8 | 36.2 | 93.3 | 23 | 37.8 | 8.4 | 4.2 |  | 1914 | 12.9 | 3.4 |
| CL | 1333.3 | 289.8 | 166.7 | 97.9 | 30.2 | 95.9 | 43.3 | 40.8 | 7 | 4.2 |  | 2084.5 | 14.1 | 4.6 |
| JS | 476.8 | 364.3 | 129.8 | 56.2 | 13.1 | 103.7 | 126 | 120.4 | 7.7 | 4.1 |  | 1924.7 | 10.6 | 3.1 |
| PR | 18.3 | 85.7 | 153.1 | 90.6 | 45.5 | 94.6 | 70.6 | 118.2 | 7.4 | 3.8 |  | 3470 | 12.4 | 5.1 |
| RA | 1258 | 105 | 186.5 | 140 | 25.5 | 85.5 | 169.7 | 77.3 | 7.2 | 4 |  | 2333.3 | 16.1 | 4.4 |
| HD | 1635.9 | 111 | 154.3 | 75 | 62.9 | 86.2 | 62.7 | 70.2 | 8.4 | 4.1 |  | 2160.9 | 13.9 | 4 |
| JF | 908.3 | 384.3 | 273.5 | 157.5 | 24.9 | 81.7 | 118 | 96.7 | 8.2 | 4.6 |  | 1931.6 | 14.6 | 4.5 |
| LM | 696.5 | 172.1 | 167.7 | 101.6 | 92.2 | 90.2 | 46 | 41.8 | 7.6 | 4.3 | 9 | 1590.2 | 12.4 | 4.7 |
| RC | 17.3 | 89.2 | 193.1 | 108.7 | 56.4 | 101.5 | 49.1 | 56.9 | 7.2 | 4 | 9.4 | 1828.9 | 13.2 | 4.3 |
| JE | 599.7 | 150 | 186 | 124.3 | 31.1 | 84.3 | 148.8 | 83.8 | 7.7 | 4.3 |  | 1244.6 | 14.5 | 2.9 |
| MP | 451 | 213.7 | 186.1 | 108.1 | 35.2 | 101.9 | 67.3 | 40 | 7.2 | 4.1 |  | 1275.4 | 14.4 | 2.6 |
| MR | 15 | 373 | 130.2 | 65.5 | 14.1 | 108.4 | 44.3 | 70.1 | 6.3 | 2.4 | 69.2 | 1452.5 | 11.3 | 3.3 |
| MEAN | 719.3 | 188.4 | 172.5 | 104.7 | 36.8 | 93 | 76.6 | 64.9 | 7.5 | 4.1 | 29.2 | 2157.4 | 13.1 | 4.265 |
| MEDIAN | 595.25 | 168.6 | 167.7 | 104.8 | 33.15 | 93.3 | 54 | 58.4 | 7.6 | 4.1 | 14.15 | 1928.15 | 13.2 | 4.35 |

Example 4

Once-weekly recombinant human erythropoietin (epoetin alpha) facilitates optimal ribavirin (RBV) dosing in Hepatitis C virus (HCV)-infected patients receiving Interferon-α-2b (IFN)/RBV combination therapy. RBV dose reduction or discontinuation has been the standard approach to treating hemoglobin (Hb) decreases resulting from IFN/RBV therapy in HCV-infected patients. A recent retrospective analysis suggested that maintaining RBV doses greater than 80% (10.6 mg/kg per day) of the recommended dose was associated with higher sustained virologic response rates (McHutchison et al., AASLD. 2000:223A. Abstract 247). An open-label, randomized, multicenter study was conducted to assess the efficacy and tolerability of once-weekly (QW) epoetin alpha therapy for hemoglobin decreases associated with IFN/RBV therapy and to evaluate the impact of epoetin alpha therapy on RBV dosing.

HCV-infected patients who developed hemoglobin levels ≦12 g/dL during the first 24 weeks of combination IFN/RBV therapy (n=60) were randomly assigned to treatment with epoetin alpha (40000 units) subcutaneously once weekly for up to 36 weeks or standard of care (SOC). The primary and secondary efficacy end points were changes from baseline (at Week 16) in hemoglobin level and RBV dose, respectively.

At baseline, mean hemoglobin levels and RBV doses were similar between the epoetin alpha and SOC groups (11.0 g/dL, for both, and 998 vs. 986 mg/day, respectively). At the last available assessment (LAST), the mean changes from baseline hemoglobin levels were +2.7 vs. +0.4 g/dL for epoetin alpha vs. SOC groups (P<0.05), respectively; and the mean changes in RBV doses were −25 and −190 mg/day, respectively (P<0.05). The last available assessment mean hemoglobin level in the epoetin alpha group (13.8 g/dL) was significantly greater (P<0.05) than that of the SOC group (11.3 g/dL). Based on the last available assessment, 77% vs. 50% (P<0.01) of patients in the epoetin alpha vs. SOC groups, respectively, were treated with RBV doses greater than 10.6 mg/kg per day.

Once weekly epoetin alpha therapy effectively increased hemoglobin levels in HCV-infected patients treated with INF/RBV. Epoetin alpha was well tolerated and increased the proportion of patients able to tolerate RBV doses greater than 10.6 mg/kg per day, which has been shown to increase the likelihood of sustained virologic response to IFN/RBV treatment.

Attached as FIG. 2 are plots of hemoglobin levels by time for 18 EPO-treated patients.

REFERENCES

1. U.S. Pat. No. 6,172,046 B1, Issued: Jan. 9, 2001 to Albrecht, "Combination Therapy for Eradicating Detectable HCV-RNA in Patients Having Chronic Hepatitis C Infection."

2. U.S. Pat. No. 5,610,054, Issued: Mar. 11, 1997 to Draper, "Enzymatic RNA Molecule Targeted Against Heptatitis C Virus."

3. U.S. Pat. No. 5,869,253, Issued: Feb. 9, 1999 to Draper, "Method and Reagent for Inhibiting Hepatitis C Virus Replication."

4. U.S. Pat. No. 6,132,966, Issued: Oct. 17, 2000 to Draper, "Method and Reagent for Inhibiting Hepatitis C Virus Replication."

5. U.S. Pat. No. 5,399,551, Issued: Mar. 21, 1995 to Ise et al., "Enhancer for the Antianemia Effect of Erythropoietin and Method of Augmenting the Antianemis Effect of Erythropoietin."

6. U.S. Pat. No. 5,604,198, Issued: Feb. 18, 1997 to Poduslo et al., "Method to Enhance Permeability of the Blood/Brain Blood/Nerve Barriers to Therapeutic Agents."

7. U.S. Pat. No. 5,670,477, Issued: Sep. 23, 1997 to Poduslo et al., "Method to Enhance Permeability of the Blood/Brain Blood/Nerve Barriers to Therapeutic Agents."

8. U.S. Pat. No. 5,661,125, Issued: Aug. 26, 1997 to Strickland, "Stable and Preserved Erythropoietin Compositions."

9. U.S. Pat. No. 6,063,772, Issued: May 16, 2000 to Tam, "Specific Modulation of Th1/Th2 Cytokine Expression by Ribavirin in ActivatedT-lymphocytes."

10. U.S. Pat. No. 5,543,390, Issued: Aug. 6, 1996 to Yatvin et al., "Covalent Microparticle-Drug Conjugates for Biological Targeting."

11. U.S. Pat. No. 5,543,391, Issued: Aug. 6, 1996 to Yatvin et al., "Covalent Microparticle-Drug Conjugates for Biological Targeting."

12. Jen F, Glue P, Gupta S, et al., *Population Pharmacokinetic and Pharmacodynamic Analysis of Ribavirin in Patients with Chronic Hepatitis C* (Therapeutic Drug Monitoring, Vol. 22, No. 3, 2000).

13. Weisz K, Goldman D, Talal A, et al., *Interferon (IFN) and Ribavirin (RBV) Therapy for Hepatitis C (HCV) in HIV-Coinfected Patients,* 12 Month Follow-Up, 7$^{th}$ Conference on Retroviruses and Opportunistic Infections, at the Birth of a Century, Research Toward Ending AIDS, Program and Abstracts, Jan. 30–Feb. 2, 2000.

14. National Institutes of Health Management of Hepatitis C Consensus Development Statement. Mar. 24–26, 1997.

15. Jelkmann W B, Fandrey J, Frede S, et al. Inhibition of erythropoietin production by cytokines: implications for the anemia involved in inflammatory states. Ann NY Acad Sci 1994;718:300–9.

16. Lai C M, Swaminathan N, Beilharz M W, et al. Interferon-α inhibits erythropoietin-induced proliferation, but not differentiation, and restricts erythroleukemia development. J Interferon Cytokine Res 1995;15:669–75.

17. Gogu S R, Beckman B S, Wilson R B, et al. Inhibitory effects of zidovudine in erythroid progenitor cells: reversal with a combination of erythropoietin and interleukin-3. Biochem Pharmacol 1995;50:413–9.

18. Goodnough L T, Anderson K C, Kurtz S, et al. Indications and guidelines for the use of hematopoietic growth factors. Transfusion 1993;33:944–59.

19. Kuehl A K, Noormohamed S E. Recombinant erythropoietin for zidovudine-induced anemia in AIDS. Ann Pharmacother 1995;29:778–9.

20. Alter M J, Kruszon-Moran D, Nainan O V, et al. The prevalence of hepatitis C virus infection in the United States, 1988 through 1994. N Engl J Med 1999;341:556–62.

21. Alter M J, Mast E E, Moyer L A, et al. Hepatitis C. Infect Dis Clin North Am 1998;12:13–26.

22. National Institutes of Health Management of Hepatitis C Consensus Development Conference Statement. Mar. 24–26, 1997. http://odp.od.nih.gov/consensus/cons105/105statement.htm.

23. Davis G L, Balart L A, Schiff E R, et al. Treatment of chronic hepatitis C with recombinant interferon alpha. A multicenter randomized, controlled trial. Hepatitis Interventional Therapy Group. N Engl J Med 1989;321:1501–6.

24. Di Bisceglie A M, Martin P, Kassianides C, et al. Recombinant interferon alpha therapy for chronic hepatitis C. A randomized, double-blind, placebo-controlled trial. N Engl J Med 1989;321:1506–10.

25. Causse X, Godinot H, Chevallier M, et al. Comparison of 1 or 3 MU of interferon alpha-2b and placebo in patients with chronic non-A, non-B hepatitis. Gastroenterology 1991;101:497–502.

26. Marcellin P, Boyer N, Giostra E, et al. Recombinant human alpha-interferon in patients with chronic non-A, non-B hepatitis: a multicenter randomized controlled trial from France. Hepatology 1991;13:393–7.

27. Thomas H C, Booth J, Brown J. Pathophysiology and treatment of hepatitis C. Drugs 1996;52(Suppl 2):1–8.

28. McHutchison J G, Gordon S C, Schiff E R, et al. Interferon alpha-2b alone or in combination with ribavirin as initial treatment for chronic hepatitis C. N Engl J Med 1998;339:1485–92.

29. Poynard T, Marcellin P, Lee S S, et al. Randomised trial of interferon alpha2b plus ribavirin for 48 weeks or for 24 weeks versus interferon alpha2b plus placebo for 48 weeks for treatment of chronic infection with hepatitis C virus. International Hepatitis Interventional Therapy Group. Lancet 1998;352:1426–32.

30. Reichard O, Norkrans G, Fryden A, et al. Randomized, double-blind, placebo-controlled trial of interferon alpha-2b with and without ribavirin for chronic hepatitis C. The Swedish Study Group. Lancet 1998;351:83–7.

31. Rebetron product label. Physician's desk reference (Edition 53). Montvale, N.J.: Medical Economics Company, Inc., 1999.

32. Reichard O, Schvarcz R, Weiland O. Therapy of hepatitis C: alpha interferon and ribavirin. Hepatology 1997;26(Suppl 1):108 S–11S.

33. Krantz S B. Erythropoietin. Blood 1991;77:419–34.

34. Moore R D, Keruly J C, Chaisson R E. Anemia and survival in HIV infection. J Acquir Immune Defic Syndr Hum Retrovirol 1998;19:29–33.

35. Fisher J W. Erythropoietin: physiologic and pharmacologic aspects. Proc Soc Exper Biol Med 1997;216:358–69.

36. Dawson-Saunders B, Trapp R G. Basic and clinical biostatistics. Norwalk, Conn.: Appleton & Lange, 1990.

37. Means R T, Jr. Pathogenesis of the anemia of chronic disease: a cytokine-mediated anemia. Stem Cells 1995;13:32–7.

38. Beguin Y. Erythropoietin and the anemia of cancer. Acta Clinica Belgica 1996;51:36–52.

39. Baer A N, Dessypris E N, Goldwasser E, et al. Blunted erythropoietin response to anemia in rheumatoid arthritis. Br J Haematol 1987;66:559–64.

40. Spivak J L, Barnes D C, Fuchs E, et al. Serum immunoreactive erythropoietin in HIV-infected patients. JAMA 1989;261:3104–7.

41. Means R T, Jr. Advances in the anemia of chronic disease. Int J Hematol 1999;70:7–12.

42. Means R T, Jr., Krantz S B. Progress in understanding the pathogenesis of the anemia of chronic disease. Blood 1992;80:1639–47.

43. Elghetany M T, Davey F R. Erythrocytic disorders. In: Henry J B, ed. Clinical diagnosis and management by laboratory methods (19th edition). Philadelphia: WB Saunders Company, 1996:617–63.

44. Koziel M J. Cytokines in viral hepatitis. Sem Liver Dis 1999;19:157–69.

45. Napoli J, Bishop G A, McGuinness P H, et al. Progressive liver injury in chronic hepatitis C infection correlates with increased intrahepatic expression of Th1-associated cytokines. Hepatology 1996;24:759–65.

46. Peeters H M, Jongen-Lavrencic M, Vreugdenhil G, et al. Effect of recombinant human erythropoietin on anemia and disease activity in patients with rheumatoid arthritis and anemia of chronic disease: a randomised placebo controlled double blind 52 weeks clinical trial. Ann Rheum Dis 1996;55:739–44.

47. Abels R I, Larholt K M, Krantz K D, al. Recombinant human erythropoietin (rHuEPO) for the treatment of the anemia of cancer. The Oncologist 1996;1:140–50.

48. Musto P, Falcone A, D'Arena G, et al. Clinical results of recombinant erythropoietin in transfusion-dependent patients with refractory multiple myeloma: role of cytokines and monitoring of erytropoiesis. Eur J Haematol 1997;58:314–9.

49. MacDougall D S. Recombinant human erythropoietin for HIV-related anemia. J

50. Harbol A W, Liesveld J L, Simpson-Haidaris P J, et al. Mechanisms of cytopenia in views 1994;8:241–51.

51 Cazzola M, Mercuriali F, Brugnara C. Use of recombinant human erythropoietin outside the setting of uremia. Blood 1997;89:4248–67.

What is claimed is:

1. A method for treating hepatitis C in an HIV-negative patient in need thereof comprising administering ribavirin (RBV) or RBV and interferon-alpha (LFN), wherein the improvement comprises administering Erythropoietin (EPO) concomitantly or sequentially or via co-administration with the RBV or with the RBV and IFN and the RBV is administered at a maximum effective dosage wherein said dosage is at or between 800–1200 mg day.

2. A method for treating ribavirin or ribavirin and interferon-alpha induced anemia in hepatitis C patients comprising administering erythropoietin to a patient in need thereof as a liquid preparation subcutaneously, parenterally, intradermally, intramuscularly or intravenously wherein the ribavirin or ribavirin and interferon-alpha induced anemia is a result of treating said hepatitis C patients with a maximum ribavirin effective dosage wherein said dosage is at or between 800–1200 mg per day.

3. A method for treating ribavirin or ribavirin and interferon-alpha induced anemia comprising administering Erythropoietin to a patient in need thereof as a suspension, emulsion, syrup or elixir wherein the ribavirin or ribavirin and interferon-alpha induced anemia is a result of treating said patient in need thereof with a maximum effective dosage of ribavirin wherein said dosage is at or between 800–1200 mg per day.

4. A method for treating hepatitis C (HCV) and for treating ribavirin or ribavirin and interferon-alpha induced anemia employed in treating said HCV in a patient in need thereof by administering erythropoietin to the patient subcutaneously for at least about six months wherein the ribavirin or ribavirin and interferon-alpha induced anemia is a result of treating said HCV in a patient in need thereof with a maximum effective dosage of ribavirin wherein said dosage is at or between 800–1200 mg per day.

5. The method of claim 4 wherein the hepatitis C is genotype 2 and/or 3.

6. A method for treating hepatitis C (HCV) and for treating ribavirin or ribavirin and interferon-alpha induced anemia employed in treating said HCV in a patient in need thereof by administering erythropoietin to the patient subcutaneously for at least about 12 months wherein the ribavirin or ribavirin and interferon-alpha induced anemia is a result of treating said HCV in a patient in need thereof with a maximum effective dosage of ribavirin wherein said dosage is at or between 800–1200 mg per day.

7. The method of claim 6 wherein the hepatitis C is genotype 1 and/or 4.

8. A method for treating hepatitis C in a patient in need thereof, comprising administering ribavirin and interferon-alpha wherein the improvement comprises co-administering to the patient subcutaneously, at a pre-determined effective amount, an Erythropoietin liquid preparation wherein the ribavirin is administered in a maximum effective dosage wherein said dosage is at or between 800–1200 mg per day.

9. The method for treating hepatitis C comprising administering ribavirin and interferon-alpha wherein the improvement as claimed in claim 8 comprises administering to patients subcutaneously at a weekly dose of about 10,000 to 70,000 units of erythropoietin.

10. The method for treating hepatitis C comprising administering ribavirin and interferon-alpha wherein the improvement as claimed in claim 8 comprises administering to patients subcutaneously at a weekly dose of about 20,000 to 60,000 units of erythropoietin.

11. The method of claim 8 wherein the patient is HIV negative.

* * * * *

(12) EX PARTE REEXAMINATION CERTIFICATE (5839th)
United States Patent
Dieterich

(10) Number: US 6,833,351 C1
(45) Certificate Issued: Jul. 31, 2007

(54) METHOD OF TREATING ANEMIA CAUSED BY RIBAVIRIN TREATMENT OF HEPATITIS C USING ERYTHROPOIETIN ALPHA

(76) Inventor: Douglas T. Dieterich, 62 St. James St., South, Garden City, NY (US) 11530

Reexamination Request:
No. 90/007,370, Jan. 7, 2005

Reexamination Certificate for:
Patent No.: 6,833,351
Issued: Dec. 21, 2004
Appl. No.: 09/862,404
Filed: May 21, 2001

(51) Int. Cl.
*A61K 38/18* (2006.01)
*A61K 38/21* (2006.01)

(52) U.S. Cl. ............................ 514/2; 514/44; 514/45; 530/385; 530/395; 530/399

(58) Field of Classification Search ....................... None
See application file for complete search history.

(56) References Cited

U.S. PATENT DOCUMENTS

| | | | |
|---|---|---|---|
| 5,399,551 A | | 3/1995 | Ise et al. |
| 6,268,336 B1 | * | 7/2001 | Niitsu et al. .................... 514/8 |
| 6,472,373 B1 | * | 10/2002 | Albrecht ....................... 514/43 |

OTHER PUBLICATIONS

Goodman and Gilman's The Pharmacological Basis of Therapeutics (8th Ed. McGraw Hill, Inc. 1990) pp. 1279–1281.*

Weisz, K.B., Braun, J.P., Dieterich, D.T., Hergenroeder, P.F., Kreiswirth, S.J., Mullen, M.P., McMeeking, A.A., Tirelli, R., "Erythropoietin use for ribavirin/interferon–induced anemia in Hepatitis C patients", [abstract], Proceedings of the 38th Interscience Conference on Antimicrobial Angets and Chemotherapy (ICAAC); Sep. 24–27, San Diego, California, 1998.

Weisz, K., Hau, T., Kreiswirth, S., McMeeking, M, Braun, J., Tirelly, J., Talal, A.H., Dieterich, D.T., "Erythropoietin use for ribavirin/interferon induced anemia in patients with Hepatitis C" [poster], Proceedings of the 38th Interscience Conference on Antimicrobial Angets and Chemotherapy (ICAAC); Sep. 24–27, San Diego, California, 1998.

Bizollon T., Palazzo, U., Ducerf, C., Chevallier, M., Elliott, M., Baulieux, J., Pouyet, M., Trepo, C., "Pilot study of the combination of interferon alfa and ribavirin as therapy of recurrent hepititis C after liver transplantation," HEPATOLOGY, (1997), 26(2):500–504, (abstract).

Dieterich D.T., "Hepatitis C Virus and Human Immunodeficiency Virus: Clinical Issues in Coinfection," The American Journal of Medicine, Dec. 27, 1999, vol. 107 (6B):79S–83S.

Dieterich D.T., Wasserman, R., Brau, N., Hasasanein, T.I., Bini, E.J., Bowers, P.J., Sulkowski, M.S., "Once–Weekly Epoetin Alfa Improves Anemia and Facilitates Maintenance of Ribavirin Dosing in Hepatitic C Virus–Infected Patients Receiving Ribavirin Plus Interferon Alfa". The American Journal of Gastroenterology, vol. 98, No. 11, (2003).

Dieterich D.T., Weisz, K.B., Goldman, D.J., Malicdem, M.L., "Combination Treatment with Interferon (IFN) and Ribavirin (RBV) for Hepatitis C (HCV) in HIV Co–Infection Patients," HEPATOLOGY, AASLD Abstract 422, vol. 30, No. 4, Pt. 2, (Oct. 1999).

Manns M.P., McHutchison, J.G., Gordon, S.C., Rustgi, V.K., Shiffman, M., Reindollar, R., Goodman, Z.D., Koury, K., Ling, M–H., Albrecht, J.K., "Peginterferon alfa–2b plus ribavirin compare with interferon alfa–2b plus ribavirin for initial treatment of chronic hepatitis C: a randomised trial," The Lancet, vol. 358, Sep. 22, 2001.

McHutchison J.G., Ware, J.E. Jr., Bayliss, M.S., Pianko, S., Alrecht, J.K., Cort, S., Yang, I., Neary, M.P., "The effects of interferon alpha–2b in combination with ribavirin on health related quality of life and work productivity," Journal of Hepatology, 34 (2001) 140–147.

Mocroft A., Kirk, O., Barton, S.E., Dietrich, M., Proenca, R., Colebunders, R., Pradier, C., Monforte, A.d'A., Ledergerber, B., Lundgren, J.D., "Anaemia is an independent predictive marker for clinical prognosis in HIV–infected patiehnts from across Europe," AIDS 1999, vol. 13:943–950.

Afdhal, N.H., Dieterich, D.T., Pockros, P.J., Schiff, E.R., Shiffman, M.L., Sulkowski, M.S., Wright, T., Younossi, Z., Goon, B.L., Tang, L., Bowers, P.J., "Epoetin Alfa Maintains Ribavirin Dose in HCV–Infected Patients: A Prospective, Double–Blind, Randomized Controlled Study," GASTROENTEROLOGY, (2004), 126:1302–1311.

Wasserman R., Brau, N., Hassanein, T.I., Bini, E., Sulkowski, M., Dieterich, D., "Once weekly epoetin alfa increases hemoglobin and decreases RBV discontinuation among HCV patients who develop anemia on RBV/INF therapy," HEPATOLOGY (Oct. 2000), AASLD Abstracts, No. 833.

Weisz, K., Kreiswirth, S., McMeeking, M., Braun, J., Tirelli, J., Talal, A.H., Dieterich, D.T., "Erythropoietin Use For Ribavirin/Interferon Induced Anemia in Patients With Hepatitis C," Hepatology, AASLD Abstract 501, (Oct. 1998).

\* cited by examiner

*Primary Examiner*—Bennett Celsa

(57) ABSTRACT

Claimed and disclosed is a new use for a previously approved drug: erythropoietin. The present invention teaches using Erythropoetin to treat anemia caused by the combined treatment of Ribavirin and alpha-interferon. Erythropoetin has previously been approved for the treatment of anemia caused by cancer chemotherapy, renal failure and HIV. It has not been used for anemia caused by ribavirin. Ribavirin is part of a two-drug regimen now used to treat hepatitis C along with alpha interferon. The principal side effect of ribavirin is a hemolytic anemia. In the past, mangement of that anemia was done by dose reduction of the ribavirin, sometimes resulting in reversal of part of the anemia. It has become particularly important in light of new data, to maximize the dose of ribavirin given to persons undergoing treatment for hepatitis C to ensure a successful eradication of hepatitis C.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

* * * * *